(12) United States Patent
Decker

(10) Patent No.: US 10,863,924 B2
(45) Date of Patent: Dec. 15, 2020

(54) SYSTEM FOR CUSTOMIZED MANUFACTURE OF WEARABLE OR MEDICAL PRODUCTS

(71) Applicant: DESMA SCHUHMASCHINEN GMBH, Achim (DE)

(72) Inventor: Christian Decker, Weyhe (DE)

(73) Assignee: DESMA Schuhmaschinen GmbH, Achim (DE)

( * ) Notice: Subject to any disclaimer, the term of this patent is extended or adjusted under 35 U.S.C. 154(b) by 150 days.

(21) Appl. No.: 16/311,101

(22) PCT Filed: Jun. 21, 2017

(86) PCT No.: PCT/EP2017/065203
§ 371 (c)(1),
(2) Date: Dec. 18, 2018

(87) PCT Pub. No.: WO2017/220638
PCT Pub. Date: Dec. 28, 2017

(65) Prior Publication Data
US 2019/0175070 A1    Jun. 13, 2019

(30) Foreign Application Priority Data

Jun. 21, 2016  (EP) ...................................... 16175501

(51) Int. Cl.
*A61B 5/107* (2006.01)
*G06Q 30/06* (2012.01)
(Continued)

(52) U.S. Cl.
CPC .............. *A61B 5/1074* (2013.01); *A43D 1/02* (2013.01); *A61B 5/0064* (2013.01);
(Continued)

(58) Field of Classification Search
CPC ........ A61B 5/0064; A01B 5/1074; A43D 1/02
(Continued)

(56) References Cited

U.S. PATENT DOCUMENTS 6,160,264 A * 12/2000 Rebiere ................ A61B 5/1074
12/1 R
6,925,350 B2 * 8/2005 Watanabe ................ A41H 1/10
33/12

(Continued)

FOREIGN PATENT DOCUMENTS

EP    1 475 222 A1    11/2004
JP    2002230357      8/2002
(Continued)

OTHER PUBLICATIONS

International Search Report dated Jul. 19, 2017 for International Application No. PCT/EP2017/065203, 4 pages.
(Continued)

*Primary Examiner* — George B Bennett
(74) *Attorney, Agent, or Firm* — Knobbe, Martens, Olson & Bear, LLP

(57) ABSTRACT

The invention relates to a system for customized manufacture of a wearable and/or medical product, said system comprising a scan unit for storing and transferring a digital representation of a body or part thereof of one or more users, a manufacturing unit of one or more providers configured to manufacture said wearable and/or medical product in accordance with geometric characteristics of said digital representation and a customized product selection platform comprising a user database, a product database and a matching and/or configurator engine. In some embodiments the invention relates to corresponding systems and methods for customized selection and production of personalized items from multiple providers using centralized user profiles based
(Continued)

Figure 1:
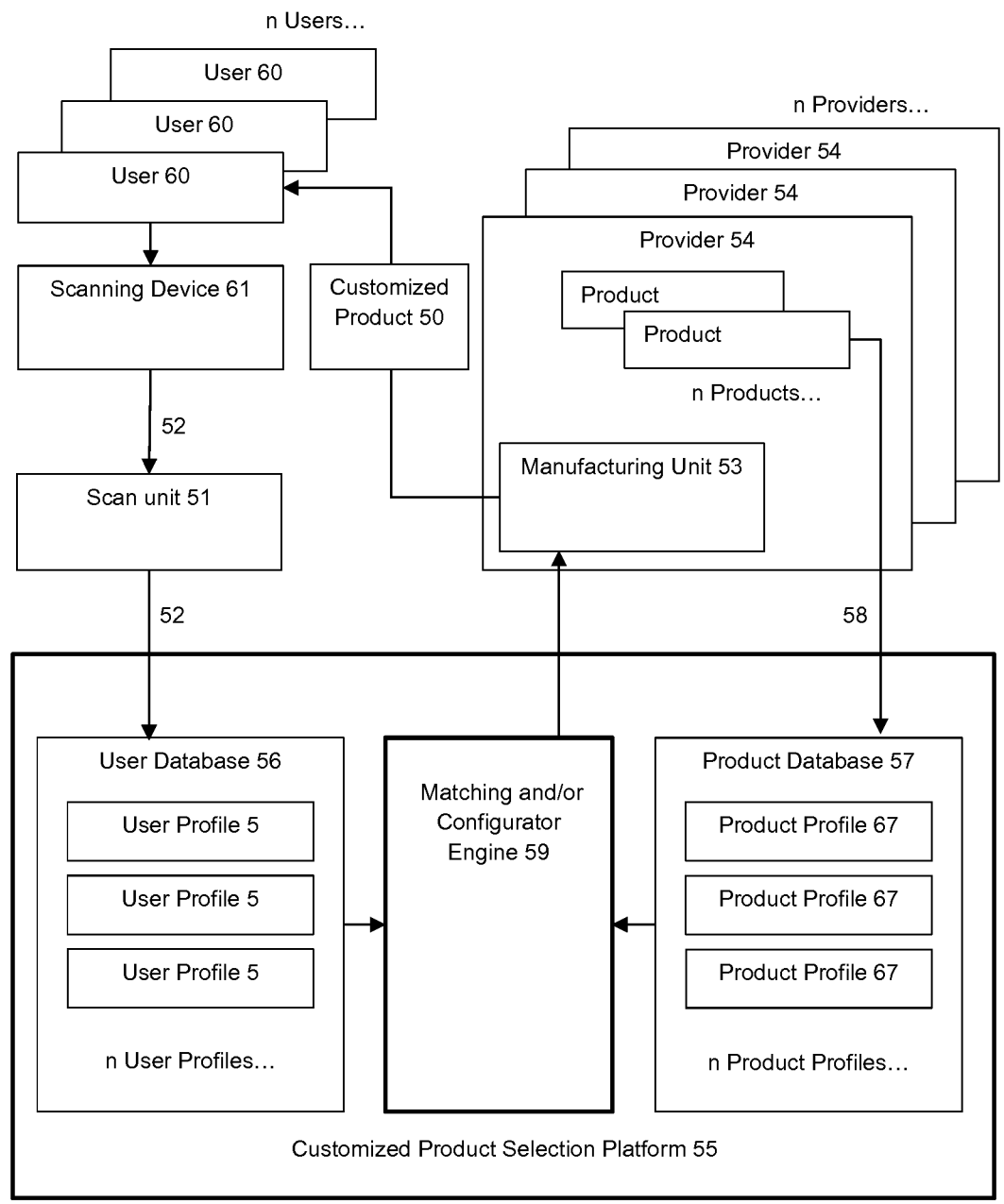

on 3D digital representations of a user's body or parts thereof.

27 Claims, 8 Drawing Sheets

(51) Int. Cl.
    *A43D 1/02*     (2006.01)
    *A61B 5/00*     (2006.01)
    *A41H 1/02*     (2006.01)
    *A61B 5/103*     (2006.01)
    *A61B 5/11*     (2006.01)

(52) U.S. Cl.
    CPC ........... *G06Q 30/0621* (2013.01); *A41H 1/02* (2013.01); *A43D 2200/60* (2013.01); *A61B 5/1036* (2013.01); *A61B 5/112* (2013.01)

(58) Field of Classification Search
    USPC .............................................. 33/6, 512, 515
    See application file for complete search history.

(56) References Cited

U.S. PATENT DOCUMENTS

| | | | | |
|---|---|---|---|---|
| 8,567,081 | B2* | 10/2013 | Smith | A61B 5/0082 33/515 |
| 2003/0065562 | A1 | 4/2003 | Matsui et al. | |
| 2004/0054752 | A1 | 3/2004 | Takagi et al. | |
| 2005/0097762 | A1* | 5/2005 | Biesbrouck | A61B 5/1036 33/3 R |
| 2009/0076772 | A1 | 3/2009 | Hinshaw et al. | |
| 2009/0234489 | A1* | 9/2009 | Healy | G06Q 30/02 700/130 |
| 2010/0058855 | A1* | 3/2010 | Tadin | A61B 5/1036 73/172 |
| 2010/0229422 | A1* | 9/2010 | Goonetilleke | A43D 1/02 36/43 |
| 2011/0099845 | A1 | 5/2011 | Miller | |
| 2011/0232008 | A1 | 9/2011 | Crisp | |
| 2014/0277658 | A1 | 9/2014 | Hanft | |
| 2014/0340479 | A1 | 11/2014 | Moore et al. | |
| 2015/0059214 | A1* | 3/2015 | Donovan | A43B 5/06 36/100 |
| 2015/0061166 | A1 | 3/2015 | Van de Vrie | |
| 2015/0332369 | A1 | 11/2015 | Nakane | |
| 2016/0000188 | A1 | 1/2016 | Hanft | |
| 2020/0107614 | A1* | 4/2020 | Walker | A43D 25/20 |
| 2020/0202406 | A1* | 6/2020 | Luh | A61B 5/6807 |

FOREIGN PATENT DOCUMENTS

| | | |
|---|---|---|
| JP | 2002288482 | 10/2002 |
| JP | 2003108846 | 4/2003 |
| JP | 004536146 | 9/2010 |
| JP | 2011197276 | 10/2011 |
| JP | 2014518098 | 7/2014 |
| JP | 2015219784 | 12/2015 |
| JP | 2016071537 | 5/2016 |
| WO | WO 2009/055451 | 4/2009 |
| WO | WO 2012/162724 | 12/2012 |
| WO | WO 2014/100462 | 1/2014 |
| WO | WO 2016/069491 | 5/2016 |

OTHER PUBLICATIONS

Written Opinion of the International Searching Authority dated Jul. 19, 2017 for International Application No. PCT/EP2017/065203, 7 pages.

Australian Office Action dated Sep. 15, 2020, for Australian Patent Application No. 2017281414. 6 pages.

* cited by examiner a b

C

SYSTEM FOR CUSTOMIZED MANUFACTURE OF WEARABLE OR MEDICAL PRODUCTS

CROSS REFERENCE TO RELATED APPLICATIONS

This is the U.S. National Phase Application, filed under 35 U.S.C. 371, of International Patent Application No. PCT/EP2017/065203, filed on Jun. 21, 2017, which claims priority to European Patent Application No. 16175501.2 filed on Jun. 21, 2016, the entire disclosure of each of which is incorporated herein by reference.

The invention relates to a system for customized manufacture of a wearable and/or medical product, said system comprising a scan unit for storing and transferring a digital representation of a body or part thereof of one or more users, a manufacturing unit of one or more providers configured to manufacture said wearable and/or medical product in accordance with geometric characteristics of said digital representation and a customized product selection platform comprising a user database, a product database and a matching and/or configurator engine. In some embodiments the invention relates to corresponding systems and methods for customized selection and production of personalized items from multiple providers using centralized user profiles based on 3D digital representations of a user's body or parts thereof.

BACKGROUND OF THE INVENTION

Mass production of wearable and medical products has been increasing rapidly since the industrial revolution and has led, on the one hand, to reduced costs for common clothing and apparel items, but on the other hand, to significant reduction in quality and specificity with respect to the exact needs of the user.

A major disadvantage of mass production is the lack of product uniqueness. It is a standardized process fulfilling many consumer needs with one solution, which often is unsatisfactory. Mass produced items may in some cases lead to unwanted medical conditions due to lack of consideration of the particular physical requirements of any given user. For example, the widespread distribution of mass manufactured shoes without consideration of the unique aspects of each user's foot can lead to medical conditions with respect to distorted gait, knee and hip pain or back problems.

Another significant disadvantage of mass production is the increased inventory or stock of products that is required before the products are provided to the end user. Overstocking occurs due to the production of many items at one time. Increased requirements on inventory lead to increased costs, due not only to the investment in space, materials and labor required for mass production, but also with respect to the wastage of mass produced items. Typical production cycles lead to manufacture of hundreds of thousands of items before distribution. Due to rapid changes in styles and production preferences a large majority of mass produced items are simply disposed of, causing significant environmental unfriendliness due to the limited capacity for recycling and the unnecessary energy cost invested in production of large numbers of items that are never used.

In light of the significant waste and lack of uniqueness incurred through large scale production of wearable and medical items, alternative technologies are required for fast and reliable customization of both consumer and medical products that enable consideration of individualized physical requirements in addition to specific individual taste and stylistic requirements.

Solutions for the manufacture of customized clothing on the basis of consumer specific physical data have been proposed (see US20080312765) but have failed until now to incorporate these technologies in a centralized, user-specific, brand-independent system for automated or semi-automated customized production.

Shoe manufacturing has a tradition of user customization via the use of specific orthotic shoe soles or in-soles in light of subject-specific foot form or motion. For example, U.S. Pat. No. 7,392,559 described a method and apparatus for manufacturing custom orthotic footbeds.

US20070039205 discloses foot measurement devices that include an optical scanner and a sensor for measuring pressure. US20090076772 describes a kiosk for obtaining foot information that is subsequently considered upon assembly of a custom built shoe. Information derived from these measurement devices is typically converted into a shoe prescription, such that a store representative is able to construct a pair of shoes made from a set of prefabricated footwear components.

US20140277658 discloses a protective patient footwear design and manufacturing system and methods. US20150061166 describes a device and a method for producing custom-made spectacles. US20140340479 discloses a system and am method to capture and process body measurements. US20090076772 describes footbeds and a method and apparatus for producing such footbeds. US20110099845 discloses customized footwear and methods for manufacturing. EP 1475222 describes an apparatus for manufacturing footwear.

Although medical conditions arising from sub-optimal gait or abnormal foot shape may be avoided by customized shoes prepared traditionally, centralized systems for rapid manufacture of customized shoes via automated means have until now not been effectively established. Furthermore, the costs, in time and expense, for each of the measurement and production-delivery phases of the above mentioned systems are high and preclude their application to a major market.

Although potential alternative technologies are in development, a significant need remains for providing effective means for addressing individual requirements with respect to customized wearable and/or medical products.

SUMMARY OF THE INVENTION

In light of the prior art the technical problem underlying the invention was the provision of improved means for producing customized wearable and/or medical products.

A further object of the invention is to enable faster production and distribution of customized products to the end user.

A further object of the invention is to reduce unwanted medical conditions caused by poorly fitting wearable and/or medical products, whilst preferably maintaining a wide range of stylistic choices from multiple providers or brands.

A further object of the invention is to provide means for reducing inventory demand for mass produced wearable and/or medical items, whilst preferably maintaining automated manufacture processes of said products.

This problem is solved by the features of the independent claims. Preferred embodiments of the present invention are provided by the dependent claims.

Therefore, the invention relates to a system for customized manufacture of a wearable and/or medical product, comprising:
- a scan unit configured for storing and transferring a digital representation of a body or part thereof of one or more users,
- a manufacturing unit of one or more providers, wherein said manufacturing unit is configured to manufacture said wearable and/or medical product in accordance with geometric characteristics of said digital representation, and
- A customized product selection platform comprising
  a) one or more computing devices,
  b) a user database comprising a digital representation of a body or part thereof of one or more users,
  c) a product database comprising a digital representation of one or more products for customization from one or more providers,
  d) a matching and/or configurator engine in the form of a computer-executable software configured for identification and selection, and optionally customization, of a product from said product database for customized manufacture according to a digital representation of a body or part thereof of one or more users, and
  e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit,
wherein the matching and/or configurator engine is configured for a comparison of geometric characteristics of the digital representation of a body or part thereof and the digital representation of one or more products stored in the product database.

The system of the invention provides a technical solution, namely the custom manufacture of a wearable and/or medical product (preferably a shoe or part thereof) to a technical problem, namely the provision of means for producing customized wearable and/or medical products, thereby improving health, comfort and well-being of the user, reducing inventory demands and achieving improved delivery times for said products.

The system as described herein is preferably characterised as a brand- or provider-independent internet platform, in which individual user profiles can be created, thereby enabling customized manufacture of personalized products from multiple providers based on a unified set of individual data, to which various third party providers/manufacturers may obtain access.

Within the user profiles different body data (such as digital representations of one or more body parts, such as those described herein) from a verified user can be stored, which will then be used for a specific selection of personalized wearable and/or medical products. The saved body data must only be obtained and stored once in a central database, to which potentially multiple customized manufacturers can gain access. The system offers improved and more precise selection of personal items for the consumer.

In preferred embodiments the digital representation of the body relates to the following preferred characteristics: body height, body weight, 3D geometries of the full body, foot geometries, head dimensions, eye separation distance, torso size and/or shape, hand geometry, movement, anatomy, physical disabilities and/or medical conditions. The system described herein may enable customized manufacture of the following wearable and/or medical products, without being limited thereto: shoes, textiles, headgear, hats, helmets, gloves, jewelry and personal supportive items, such as glasses, hearing aids or prosthetics. Any embodiment of the invention described herein with respect to a "product" also relates to that embodiment in the context of any one or more specific "products" as mentioned herein.

In preferred embodiments the digital representation of the body relates to the following preferred geometric characteristics: body height, 3D geometries of the full body, foot geometries, head dimensions, eye separation distance, torso size, torso shape, hand geometry, and/or anatomy.

The term "geometric characteristics" may also refer to individual specific physical properties of the user's body, such as foot pressure, gait, height, girth, body shape and/or weight.

It may also be preferred that the term "geometric characteristics" refers to the foot shape, form, and/or motion, such as pronation and/or supination.

In particular, the term "geometric characteristics" may comprise additional data on the user's body weight, body sway, limb length discrepancy, gait cycle events, pronation and supination events and body mass migration.

The comparison of geometric characteristics of the user data to the product data may be conducted using any given appropriate software, as described herein or according to the knowledge of a skilled person.

In preferred embodiments medical products relate to, without limitation, shoes, prosthetics, hearing aids, glasses and helmets. In preferred embodiments wearable products relate to, without limitation, shoes, glasses, helmets, apparel or garments, such as shirts, pants, jackets, skirts, dresses or other clothing items, hats, jewelry or gloves.

In preferred embodiments, detailed scans of foot shape, form, motion, such as pronation or supination, and/or human body movement are obtained and a manufacturing data file is produced based on said data. Manufacturing processes and methods are provided which enable production of various human individual wearable and medical products based on individualized body data of the user.

The products to be customized and produced relate preferably to medical products, which enable addressing individual specific physical properties of the user's body, such as foot pressure, gait, height, or weight. Especially for medical products, the individual scan and corresponding manufacturing data, processes and methods address individual medical needs, thereby providing a technical solution to a medical/technical problem.

Besides consideration of the physical human body, in some embodiments the invention allows products that can be designed individually by augmented reality software based on a set of configuration parameters. These configuration parameters will be based on different materials and designs, colors and/or styles, which are enabled via the customized manufacturing processes and methods described herein.

In preferred embodiments the product database comprises an electronic representation of one or more of said products for customization. Additionally, it may be preferred that the electronic representation comprises a product profile comprising information on customizability of the product which are selected from a group comprising size, shape, density, softness, form, texture, colour or weight of the product or parts thereof.

In one embodiment the system as described herein is characterized in that the scan unit is a computing device upon which a digital representation of a body or part thereof of one or more users is stored and transmitted to the user database. In particular, geometric characteristics of a digital representation of a body or part thereof of one or more users may be stored within and transmitted to the user database.

The scan unit is defined in preferred embodiments by the presence of scanned data and the capability of the unit to transmit said data to a database of multiple users. A device for scanning a body or part thereof is not a limiting aspect of the scan unit of the present invention. The scan unit may therefore represent a personal computer or other computing device upon which scanned data are stored, wherein the unit is configured for transmission of the data to the user database.

In a preferred embodiment the scanned data may be present as one or more data files that comprise a digital representation of a user's body or part thereof. The digital representation of a body or part thereof that are used by the invention can employ any kind of file format which is used in the scanning industry. For example, the digital representations can be stored in a proprietary format, DXF format, XML format, or other format suitable for storing preferably 2D or 3D information on a user's body.

In one embodiment the system as described herein is characterized in that the scan unit comprises a scanning device configured for generating a 2D or 3D digital representation of essentially the entire body, or part thereof, of a user, such as a 3D optical scanner for recovering the external 3D shape of the user's body or part thereof.

The scanning device may be configured with respect to its dimensions to be suitable for acquiring imaging or other suitable scanned data of the users body, in particular of dimensions suitable for acquiring data on the foot, essentially entire body, torso, head, head and neck, ears, internal and/or external representations of a user's ears, hands, arms, arms with or without hands, legs, legs with or without feet.

In a preferred embodiment the scanned data enables analysis of the user's body or parts thereof via representation and/or analysis of cross section, slice area, surface area, and/or volume of the 3D data obtained. In a preferred embodiment the digital representation of the body, or part thereof, of a user comprises or consists of one or more computer data files comprising information that represents a cross section, slice area, surface area, and/or volume obtained from 3D data of the body, or part thereof, of a user. Particular scanning devices are described in more detail herein.

In one embodiment the system as described herein comprises a manufacturing unit of one or more providers, wherein said manufacturing unit is configured to manufacture said wearable and/or medical product in accordance with geometric characteristics of said digital representation. The manufacturing unit may be present within the system due to physical proximity or may be geographically separated from the remaining components of the system. The manufacturing unit may in some embodiments not represent an essential component of the invention. In one embodiment the system as described herein does not comprise directly a manufacturing unit of one or more providers, but comprises the technical means for transmitting ordering information to one or more manufacturing units of said one or more providers.

The manufacturing unit relates to any device suitable for preferably automated or semi-automated manufacture of a wearable or medical product using the data comprising or corresponding to a digital representation of the user's body or part thereof provided from the user database.

In one embodiment the manufacturing unit is present in geographical or physical proximity to the scanning unit. For example, the system may comprise both a scan unit, preferably comprising a scanning device, and a manufacture unit in the same geographical location, i. e. at the same address, in the same building or in the same room as the scan unit and/or scanning device.

As used herein the term "provider" refers to any given entity capable of manufacturing a wearable and/or medical product in accordance with geometric characteristics of said digital representation. For example, the provider may preferably relate to an individual or company active in the automated manufacture of wearable and/or medical products, such as a provider of footwear with customized automated or semi-automated manufacturing capabilities based on personalized data.

In a preferred embodiment the system comprises at least two or more providers, each provider comprising one or more shoe manufacturing units.

In a preferred embodiment the system comprises multiple manufacturing units, preferably from multiple independent providers.

In preferred embodiments the providers are geographically dispersed from one another.

In some embodiments the number of manufacturing units, or providers, potentially independent from one another, are 1 to 100,000, preferably 1 to 10,000, for example 2 to 1,000, or in other embodiments, a number of providers from a minimum of 1, 2, 3, 4, 5, 6, 7, 8, 9, 10, 20, 30, 40, 50, 100, 200 or 500 to a maximum number of providers of 100, 200, 300, 400, 500, 1,000, 2,000, 5,000 or 10,000.

The system therefore provides improved means for customized product production by enabling multiple providers to offer customized products to a user, thereby enabling fast, more efficient and more closely matched product production for the individual needs of the user.

In a preferred embodiment the presence of multiple manufacturing units, preferably of multiple independent providers leads to an enhanced production of products that enable a medical or therapeutic effect with the end user, such that a technical effect is evident through the improved physical state of the end user. This improvement in well-being, such as a medical effect, is enabled by the ability to select customized products of multiple types and configurations from said multiple providers, thereby improving the fit/match of the product and speed of provision of the product.

This advantage is in particular achieved by the use of geometric characteristics of the digital representation of a body or part thereof enabling for a geometric matching of the digital representation of a body or part thereof of a user and the products stored in the product database. It is preferred that making use of geometric characteristics of the digital representation of a body or part thereof in the context of the matching of the digital representation of a body or part thereof of a user and the products stored in the product database is referred to as geometric matching. Geometric matching is associated with the following technical advantages, such as enhanced matching of individual body dimensions and products whose properties may be stored in a product database, reduced computing power for the matching and quicker provision of the product to the user. The scale of the system is also adjustable, such that with larger numbers of providers improved technical or medical effects are achieved in supplying the correct customized goods to the user in an improved or more efficient manner.

The invention may incorporate one or more features of the following preferred system or method, namely a system or method operable on one or more computing devices for manufacturing a customized wearable and/or medical product, comprising:
- providing 2D or 3D body measurements of a user using a preferably non-contact body scanner;
- providing a user with a plurality of digital product designs, preferably obtained from a product database, from which the user may select a particular product design,
- adapting the selected product via a configuration engine to the user's body measurements to obtain a customized design, for example via incorporating user style and/or fit preferences in the customized design to obtain a personalized custom-fit design;
- generating a digital pattern for a wearable and/or medical product based on the personalized custom-fit design; and/or
- manufacturing the personalized custom-fit product from the digital pattern using an automated or semi-automated manufacturing process.

In other preferred embodiments an automated system for the customized production of a wearable and/or medical product is provided, the system comprising one or more of the following features:
- a scanning device configured for obtaining a scan comprising a 2D or 3D model of a customer's body shape, or shape of a part thereof, preferably a foot;
- a computer comprising memory, an input device, a processor, a network connection, and a computer-readable storage medium having computer instruction code or software comprising:
- sizing algorithms for extracting sizing parameters from the user's scan data and scaling a digital representation of a product obtained from a product database to the user's digital representation of their body or part thereof; in particular to geometric characteristics of the user's digital representation of their body or part thereof;
- customization algorithms for enabling a user to select and incorporate fit and style preferences into the digital pattern; and
- visualization algorithms for visualizing, preferably in real time, the fit of the product with said digital representation of the user's body or part thereof derived from the scanner, wherein preferably the user may interact with and modify design parameters and wherein the digital representation of the user's body or part thereof is preferably related to geometric characteristics of said representation; and
- a product database comprising a set of digital design patterns (digital representations of products) contributed by providers; and/or
- an automated manufacturing system comprising manufacturing equipment and material handling equipment connected or networked to a controller, in which the data regarding user product selection and/or scanned body data are transmitted or considered during execution of manufacturing enabling the manufacture to occur in accordance with said data, in particular geometric characteristics of said data.

As used herein the term "manufactured in accordance with" refers to the customized manufacture of a wearable and/or medical product on the basis of the user's digital representation of their body or parts thereof, including, but not limited to, manufacture of a product of the correct properties, such as size, shape, density, softness, form, texture, colour or weight of the product or parts thereof, wherein said properties match the digital representation of the user's body or part thereof. It is preferred that the matching is based on geometric characteristics of the digital representation of the user's body or part thereof. A geometric matching is particularly advantageous as individual medical conditions of an individual user may be taken into account when identifying, selecting and/or customizing products or parts thereof from the product database. Thereby, the risk of poorly fitting wearable and/or medical products can significantly be reduced, whilst preferably maintaining a wide range of stylistic choices from multiple providers or brands.

In a preferred embodiment the manufacture of said wearable and/or medical product in accordance with geometric characteristics of said digital representation is characterised in that a physical and/or medical benefit is achieved by for the user by the customized production. The customized production thereby enables a technical effect with respect to enhancement of physical and/or medical properties of the user. Examples of these technical effects are provided in detail below.

In a preferred embodiment the manufacture of said wearable and/or medical product is automated or semi-automated, such that suitable computer programs and/or software modules are applied to direct and/or control manufacturing processes under consideration of the data received from the user database. Examples of particular solutions for manufacturing a wearable and/or medical product in accordance with geometric characteristics of a digital representation of a user's body are provided herein.

In a preferred embodiment the system of the present invention is characterised in that the customized product selection platform is a data communication and processing system. In a preferred embodiment the platform comprises additionally of a (one or more) wearable and/or medical product database (product database), wherein said product database comprises an electronic representation of one or more of said products for customization, preferably from one or more providers.

Said electronic representation may be referred to as or stored in a product profile, for example the module product profile described in the examples below, comprising information on customizability of the product, size, shape, density, softness, form, texture, colour or weight of the product or parts thereof. In other words, it is preferred that the electronic representation comprises a product profile comprising information on customizability of the product which are selected from a group comprising size, shape, density, softness, form, texture, colour or weight of the product or parts thereof.

The product profile is in a preferred embodiment accompanied by a manufacturing or production profile, for example the module production profile described in the examples below, which comprises information and/or instructions for manufacture of a particular product, with respect to machine control or instructions for carrying out automated or semi-automated manufacture on an appropriate manufacturing device.

The product database comprises in preferred embodiments basic information presented in unified form on the products offered by each of the providers, such as size, shape, density, softness, form, texture, colour or weight of the product or parts thereof that are available in light of the customizable manufacturing capabilities of the provider.

In further preferred embodiments the communication and processing system comprises additionally a matching and/or configurator engine in the form of a computer-executable software (module) configured for virtual identification, customization and/or selection of said product from said product database for customization according to a digital representation of a body or part thereof of one or more users.

In some embodiments the customized product selection platform comprises the core software modules (one or more of 1, 2, 3, 4, 5, 9, 10 and/or 12), and optionally the optional core modules as described herein (one or more of 6, 7, 8, 11, 12, 13, 14 and/or 15), according to tables 1, 2 and/or 3. In some embodiments the peripheral modules of table 1 (one or more of 16, 17, 18, 19, 20, 21 and/or 22) are also encompassed by the Customized Product Selection Platform. In preferred embodiments, the customized product selection platform also comprises the user and product databases.

In preferred embodiments the user database comprises the user profiles. In preferred embodiments the product database comprises the product profiles and/or production profiles.

In some embodiments the matching and/or configurator engine comprises the core software modules (one or more of 1, 2, 3, 4, 5, 9, 10 and/or 12), and optionally the optional core modules as described herein (one or more of 6, 7, 8, 11, 12, 13, 14 and/or 15), according to tables 1, 2 and/or 3. In some embodiments the peripheral modules of table 1 (one or more of 16, 17, 18, 19, 20, 21 and/or 22) are also encompassed by Matching and/or configurator engine. In some embodiments the Matching and/or configurator engine comprises the user database that comprises the user profiles and/or the product database that comprises the product profiles and/or production profiles.

The electronic representation of one or more of said products for customization may in preferred embodiments also include 2D or 3D digital representations of said products that may be assessed by said user. For example comparisons between the 2D or 3D representation of the user's body or parts thereof with the 2D or 3D representation of the product may be conducted, either manually or automatically, such as in virtual "trying on" of a product, or the data of the product stored in the product database and assessed by the matching and/or configurator engine may be accounted for by computer processing capabilities automatically during selection and customization of the product.

In one embodiment the user may be provided with a digital representation of said product, wherein said digital representation is preferably displayed in three dimensions and being moveable so as to show what said clothing might look like from different angles or points of view. Said user may also be provided with a representation of a virtual person, preferably representative of their body shape in accordance with said estimated body measurements, wearing said made to order product in accordance with said pattern data, said virtual person preferably being presented in three dimensions and preferably being moveable so as to demonstrate by way of review what said product might look like in use. In particular, the representation of the virtual person may be related to geometric characteristics of the body of a user or parts thereof. Preferably, the representation of the virtual person represents the body shape of a user or the shape of a body part of a user in accordance with said estimated body measurements, in particular geometric characteristics of said estimated body measurements.

In a preferred embodiment the system of the present invention is characterised in that the user database and/or scan unit comprising the digital representations of the body or part thereof of a user comprise additionally for each user a user profile. In particular, it is preferred that the user database and/or scan unit comprises geometric characteristics of the digital representations of the body or part thereof of a user.

In preferred embodiments the user profile comprises information on one or more aspects of the user selected from: physical and/or geometric characteristics of the user's, such as height, weight, girth, and/or body shape, previous product selection and/or interest, purchasing history, past and/or present location, a user identification number, delivery address, preferred colors, brands and/or price ranges, language, physical activity and/or medical conditions.

In preferred embodiments the user profile comprises at least a digital representation of the user's body or part thereof, preferably 2D or 3D, more preferably a 3D representation of the user, preferably as described by the various scanning techniques described herein.

In preferred embodiments the user profile comprises at least information on physical activity and/or medical conditions of the user. Via consideration of these characteristics, preferably physical and/or geometric characteristics, of the user in the form of a user profile the system solves a technical and/or medical problem by enabling selection and customized manufacture of wearable and/or medical products that exhibit a physical and/or medical effect on the user. The presence of information on physical activity and/or medical conditions of the user in the user profile of the present invention therefore represents a technical feature of the invention suitable for contributing to the solution of a technical problem.

In a preferred embodiment the system of the present invention is characterised in that the customized product selection platform, preferably in the form of a data communication and processing system, comprises additionally one or more computer-executable software modules configured for conducting ordering, payment and/or delivery procedures between said users and providers. The system of the present invention may in some embodiments comprise an "online shop", enabling ordering, payment and delivery of the customized product. Online payment modules, incorporating credit card or "Paypal" or similar electronic or online payment mechanisms, are known to a skilled person.

In a preferred embodiment the system of the present invention is characterised in that the customized product selection platform, preferably in the form of a data communication and processing system, comprises additionally one or more computer-executable software modules configured for providing product suggestions according to popularity of purchases and/or product interest by other users (trending).

In a preferred embodiment suggestions for products based on earlier purchases or product interest are preferably selected and/or ranked according to information in the user profile, such as age, past and/or present location, previous purchases, preferred colors, brands and/or prices.

In a preferred embodiment the system of the present invention is characterised in that the customized product selection platform, preferably in the form of a data communication and processing system, comprises additionally one or more computer-executable software modules configured for providing product suggestions according to similarity in products to those according to previous product selection and/or interest of the user, wherein said suggestions are preferably selected and/or ranked according to information in the user profile, such as age, past and/or present location, preferred colors, brands and/or prices.

In a preferred embodiment the system of the present invention is characterised in that the customized product selection platform, preferably in the form of a data communication and processing system, comprises additionally one or more computer-executable software modules configured for data and/or message transmission (exchange) between multiple users and/or providers (messaging) and/or data and/or message transmission to social media platforms.

In a further aspect the invention relates to a computer-implemented method for selection of a wearable and/or medical device for customized manufacture, comprising:
providing a digital representation of the body, or part thereof, of one or more users in a scan unit in the form of a computing device, said device being configured for storing and transmitting said representation,
transmitting said digital representation of a body, or part thereof, to a user database comprised by a customized product selection platform, wherein said platform comprises:
a) one or more computing devices,
b) a user database comprising a digital representation of a body or part thereof of one or more users,
c) a product database comprising a digital representation of one or more products for customization from one or more providers,
d) a matching and/or configurator engine in the form of a computer-executable software configured for identification and selection, and optionally customization, of a product from said product database for customized manufacture according to a digital representation of a body or part thereof of one or more users, and
e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit, and
transmitting a product selection from said platform to a manufacturing unit of one or more providers, wherein said manufacturing unit is configured to manufacture a wearable and/or medical product or part thereof in accordance with geometric characteristics of the digital representation of a body or part thereof of a user,
wherein the matching and/or configurator engine is configured for a comparison of the geometric characteristics of the digital representation of a body or part thereof and the digital representation of one or more products stored in the product database.

In a preferred embodiment the method described herein comprises generating a digital representation of a user's body, or part thereof, using a scanner configured for generating a 2D or 3D digital representation of a the body or part thereof, such as a 3D optical scanner for recovering the external 3D shape of a body or part thereof of the user.

In a preferred embodiment the method described herein comprises manufacturing a wearable and/or medical product or part thereof in accordance with geometric characteristics of said digital representation.

In a preferred embodiment the invention relates to a system as described herein, wherein the customized product selection platform comprises one or more computer-executable software modules configured for recording and preferably analyzing information on user location, user interest (as used herein according to pre-entered values by the user and/or by recording the products assessed for customization on the platform), orders and/or customization selections of one or more users, identifying trends in said information in the form of correlations between products for customized manufacture and data from the user profile, and making suggestions to a user (for purchase) and/or to a provider of customizable products (for preparation of manufacture) according to said correlations.

In a preferred embodiment the information obtained over user behavior from the system, in particular information in the form of data comprising correlations between user behavior and particular information on user location, interest, orders and/or customization selections, or correlations between user behavior and data from sources external to the essential components of the system, such as news feeds, information on local events, such as sports events, musical events, from weather services and/or forecasts, market trends, shopping or style trends and/or medical trends, is transmitted to one or more providers and/or the manufacturing units thereof in order to prepare for production of particular customized products.

For example, in case of major social events, such as sports or promotion events in the geographical proximity of any given user, increasing traffic can be localized and assigned to the specific event. The analytics module therefore enables the general performance of the website/platform to be analyzed to ensure the best possible performance for the user. All collected data may preferably be summarized into reports in order to find out where the potential for improvement of the platform is. Connected partner companies (providers) can in some embodiments use the collected data to analyze purchase of goods and/or for preparation of production of particular products.

In one embodiment the customized product selection platform of the system is characterized by an analytics module. In a preferred embodiment the analytics module is characterized in that the location, interest, orders and/or customization selected by one or more users (preferably multiple users) is recorded and trends are identified therein, preferably in the form of correlations between particular products for customized manufacture and particular user profile data, and wherein said information is considered by an analytics software module. This module preferably functions in combination with user information and product information from the respective profiles. The analytics module preferably is configured to make suggestions of customizable products to the user and/or to one or more providers on the basis of the data collected. The module may provide proposals on product selection in light of correlations between user location, interest, orders and/or interests or other user data, such as body data.

In one embodiment the customized product selection platform of the system is characterized by a prediction module. In a preferred embodiment the prediction module is characterized in that the location, interest, orders and/or customization selections of one or more users (preferably multiple users) is recorded and trends are identified therein, preferably in the form of correlations between particular products for customized manufacture and particular user profile data. This information is considered by a prediction software module, preferably in combination with user information and product information from the respective profiles, that is configured to make suggestions of customizable products to the user and/or to the provider in light of developing ordering trends.

The prediction module may in some embodiments be configured to provide proposals on product selection to either users or providers in light of correlations between user location, interest, orders and/or interests or other user data, such as body data, when compared to "global" trends identified either by traffic on the system and/or by other data sources, such as big data. For example, purchasing trends may be obtained from sources outside the essential features of the system and "fed into" the system in order to enable identification of users that show a tendency in their system usage that indicate particular preferences with respect to upcoming system usage and product selection.

In one embodiment the predictions and/or analytics module is configured to incorporate data from sources external to the essential components of the system as described herein, for example the analytics module may incorporate data from news feeds, information on local events, such as sports events, musical events, from weather services and/or forecasts, market trends, shopping or style trends and/or medical trends, wherein the term trend is defined as a general direction in which a particular behavior of one or more individuals is developing or changing, preferably wherein such trends represent multiple individuals behaving in a similar way. Such data may be processed by the prediction module and product suggestions or other system parameters may be sent to users and/or providers. In one embodiment correlations are made drawn between user behavior in the system and external data and said correlations are transmitted to providers in order to prepare for manufacture of any given customizable wearable and/or medical product.

In the present invention the term "big data" represents data sets acquired from large numbers of multiple individuals or entities from which particular trends may be derived. Typically, big data sets are so large that traditional data processing applications, such as those based on personal computers, are inadequate. The term "big data" includes the analysis, capture, data curation, search, sharing, storage, transfer, visualization, querying, updating of large population data sets, with potential considerations regarding information privacy of any given object from which data has been obtained, i. e. the user of the system.

The term big data refers preferably to the use of predictive analytics or certain other methods to extract value, information or other correlations from data. Accuracy in big data may lead to more confident decision making, and better decisions can result in greater operational efficiency, cost reduction and reduced risk. Analysis of large data sets can find new correlations to spot business trends, purchasing trends, stylistic trends and/or medical or health trends. Comparison of such big data trends with user profile information may enable more fitting proposals to the user in the context of the present system, thereby enhancing the user experience and use of the customized end product.

Embodiments Relating to Computer Implementation

The present invention is, in preferred embodiments, characterised as a centralized system, referring to a computer implemented system in which a unified, centralized user database exists, to which providers and their manufacturing equipment may be connected in order to enable customized manufacture based on the personalized information comprised within the user database. The centralized system may also comprise a product database comprising unified digital representations of products from multiple brands (providers).

The system of the invention may in some embodiments comprise one or more conventional computing devices having a processor, an input device such as a keyboard or mouse, memory such as a hard drive and volatile or non-volatile memory, and computer code (software) for the functioning of the invention. The computers may also comprise a programmable printed circuit board, microcontroller, or other device for receiving and processing data signals such as those received from the local controllers, programmable manufacturing equipment, programmable material handling equipment, and robotic manipulators.

The system may comprise one or more conventional computing devices that are pre-loaded with the required computer code or software, or it may comprise custom-designed hardware. The system may comprises multiple computing devices which perform the steps of the invention. In certain embodiments, a plurality of clients such as desktop, laptop, or tablet computers can be connected to a server such that, for example, multiple users can enter their orders for personalized products at the same time. The computer system may also be networked with other computers over a local area network (LAN) connection or via an Internet connection. The system may also comprise a backup system which retains a copy of the data obtained by the invention. The data connections of step e) may be conducted or configured via any suitable means for data transmission, such as over a local area network (LAN) connection or via an Internet connection, either wired or wireless.

A client or user computer can have its own processor, input means such as a keyboard, mouse, or touchscreen, and memory, or it may be a dumb terminal which does not have its own independent processing capabilities, but relies on the computational resources of another computer, such as a server, to which it is connected or networked. Depending on the particular implementation of the invention, a client system can contain the necessary computer code to assume control of the system if such a need arises. In one embodiment, the client system is a tablet or laptop. For example, a customer in a retail store can be given a tablet for placing an order and visualizing the personalized product to be customized/manufactured. The tablet or laptop computer can be in wireless communication with the server, which would accept and process the order.

The components of the computer system may be conventional, although the system will typically be custom-configured for each particular implementation. The computer system may run on any particular architecture, for example, personal/microcomputer, minicomputer, or mainframe systems. Exemplary operating systems include Apple Mac OS X and iOS, Microsoft Windows, and UNIX/Linux; SPARC, POWER and Itanium-based systems; and z/Architecture. The computer code to perform the invention may be written in any programming language or model-based development environment, such as but not limited to C/C++, C#, Objective-C, Java, Basic/VisualBasic, MATLAB, Simulink, StateFlow, Lab View, or assembler. The computer code may comprise subroutines which are written in a proprietary computer language which is specific to the manufacturer of a circuit board, controller, or other computer hardware component used in conjunction with the invention.

In certain embodiments of the invention, a human monitor may be present to oversee the scanning and/or manufacturing processes and to resolve any errors or faults. Nevertheless, in preferred embodiments of automated or semi-automated manufacture the monitor will not be substantially participating in the manufacture and therefore will not routinely need to move or feed work pieces or operate the manufacturing equipment.

The digital design patterns which are used by the invention as digital representations of human bodies or parts thereof or products can employ any kind of file format which is used in the industry. For example, the digital representations of products or users can be stored in a proprietary format, DXF format, XML format, or other format for use by the invention. Any suitable computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, cloud storage or a magnetic storage device.

The present invention is described below with reference to flowchart figures and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions, such as by modules. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

Embodiments Related to a Foot/Shoe Manufacture

In a preferred embodiment the present invention relates to a system and method as described herein, wherein said wearable and/or medical product is a shoe.

In a preferred embodiment the present invention relates to a system as described herein, wherein the wearable and/or medical product is a shoe, said system comprising:
  a scan unit configured for storing and transferring a digital representation of a foot or part thereof of one or more users,
  a shoe manufacturing unit of one or more providers, wherein said shoe manufacturing unit is configured to manufacture a shoe or part thereof in accordance with geometric characteristics of said digital representation, and
  A customized product selection platform comprising
    a) one or more computing devices,
    b) a user database comprising a digital representation of a foot or part thereof of one or more users,
    c) a product database comprising a digital representation of one or more shoes for customization from one or more providers,
    d) a matching and/or configurator engine in the form of a computer-executable software configured for identification and selection, and optionally customization, of said shoes from said product database for customized manufacture according to a digital representation of a foot or part thereof of one or more users, and
    e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit wherein the matching and/or configurator engine is configured for a comparison of the geometric characteristics of the digital representation of a foot or part thereof of one or more users and the digital representation of one or more shoes stored in the product database.

In one embodiment the system as described herein is characterized in that the scan unit is a foot scan unit and comprises a foot scanner configured for generating a 2D or 3D digital representation of a foot, in particular geometric characteristics of a foot or parts thereof. The term "geometric characteristics of a foot or parts thereof" may relate to characteristic lengths of the 2D or 3D digital representation of a foot, to foot pressure values, pronation, supination, outer foot outlines, outer boundaries of the feet, inner foot outlines, weight-bearing areas of the feet, sizes and/or lengths of the ankle, subtalar and midtarsal joints, size and/or lengths of anatomical deformities of the forefoot, e.g. "forefoot *varus*" or "forefoot valgus". The foot pressure values may be obtained by measurements carried out under under the heel, arch, metatarsals, and phalanges of a user's foot.

In preferred embodiments for obtaining a foot scan a 2D flatbed scanner or pressure-sensing mat is employed. In some embodiments scanners such as described in US 20110099845 may be employed.

Foot pressure mapping typically utilizes sensors to measure the contact pressure between the foot and ground or another surface. One embodiment of a foot pressure mapping system utilizes a thin pad of any size and shape. In one embodiment, the pads are composed of a matrix of small sensors and a cover. In another embodiment, the pressure mapping pads are foot shaped. When an individual stands on the pad, the sensors measure pressure at locations under the foot. The data obtained from the pressure mapping sensors reflect pressures under the heel, arch, metatarsals, and phalanges. The data is obtained and then transmitted to a memory storage unit, which can be internal or external to the pad. Pressure is measured as force per unit area in a specific location. The data is transmitted to a storage device connected to the pad. In one embodiment, the storage device is an internal component of the retailer terminal computer.

2D foot scans as described in US 20090208113 A1 may also be applied, for example methods that identify outer foot outlines defining outer boundaries of the feet of a user, and inner foot outlines defining weight-bearing areas of the feet in a computer-readable image of the feet.

A 3D optical scanner for recovering the external 3D shape of a foot may in some embodiments be employed. In some embodiments scanners such as those available from Vorum (3D Plantar Scanner, or Yeti scanner) or from Human Solutions (Footln3d) may be employed. For example, the Footln3d enables precise measurements, such as an essentially exact three-dimensional imaging of the human foot, a measuring range of 180 mm height, 180 mm width and 400 mm depth in a scan time of approx. 5-15 seconds. The measurement principle relates to optical triangulation (laser technology, safe for the eyes), and enables the following export formats: XML, CSV, OBJ, STL, eight laser sensor heads, density of points of 35 points/cm2, a tolerance of <1 mm, floor space requirements: around 1 m2, a total weight: around 30 kg and direct integration with Anthroscan for body dimension analysis.

In one embodiment a device for measuring and recording a dynamic representation of the walking or running behavior of a user may be incorporated in the system of the invention, wherein said walking or running behavior relates to pronation and/or supination. One example of such a device relates to a scanning device as described in US 20070039205. Preferably scanners may be applied that incorporate a scanner designed to provide both static and dynamic measurements of the user's foot. For example, a seat is situated such that a customer may place their feet on the foot measuring device in a relaxed non-load bearing state. Static weight-bearing measurements may then be taken as the customer stands on the measuring device. Dynamic measurements may be taken by the customer placing his or her left foot on the device while stepping through the station in one direction, and then placing a right foot on the device while stepping through the station in an opposite direction.

Complex motions called "pronation" and "supination" include motions with respect to the ankle, subtalar and midtarsal joints. Pronation includes dorsiflexion, abduction and eversion; supination includes plantar flexion, adduction and inversion. During pronation, dorsiflexion is prominent at the ankle joint, eversion at the subtalar joint and abduction at the forefoot or phalanges; during supination, plantar flexion is prominent at the ankle joint, inversion at the subtalar joint and adduction at the forefoot. Many individuals have certain anatomical deformities of the forefoot. Two of these deformities, called "forefoot *varus*" or "forefoot valgus", effect foot position during walking or running (i.e., through the gait cycle). The invention is therefore capable of adjusting the shoe in light of such conditions in order to provide comfort and health to the user. Methods of production are known to a skilled person.

Such measuring devices as described in US 20070039205 relate preferably to a foam mat equipped with a plurality of electrostatic and pressure sensors, which enable digitization of the 3D form of the foot. With such a mat, the foam conforms to the contours of the customer's plantar region to provide actual three dimensional measurements of the customer's foot. Using such a foam mat, motion, velocity, mass and 3d surfacing can be evaluated for the customer to select a particular footwear component in accordance with an embodiment of the present invention.

In further preferred embodiments the scanning device of the present invention may acquire data on the user's body weight, body sway, limb length discrepancy, gait cycle events, static 2D and 3D imaging, dynamic 2D and 3D imaging, pronation and supination events and body mass migration.

In one embodiment a device for measuring and recording a dynamic representation of the walking or running behavior of a user may be incorporated in the system of the invention, wherein said walking or running behavior relates preferably to pronation and/or supination, wherein said events are detected by a plantar pressure sensor device. Commercial technologies for plantar pressure assessment including the Emed Sensor Platform and Pedar Insole System by Novel Electronics, Inc.; F-Scan System by Tekscan, Inc.; and the Musgrave Footprint System by WM Automation and Preston Communication, Ltd. In these technologies, a fine grain matrix array of sensors measures force when the foot contacts the sensor, thereby enabling a digital representation of dynamic characteristics of the user's foot and gait whilst running or walking.

In further embodiments, the scanning products of RSscan International NV, Belgium may be employed. For example, a full foot 3d scanner (Tiger 3D scanner) may be used to create a detailed 3D scan of the user's foot, up to the ankle, to perform additional analyses on the shape and form of the feet. Such scanners provide a 3D-visualisation of the foot, including automated arch height, length and width calculation of the foot. Further suitable devices are the Footscan® systems and associated software. Further geometric characteristics of the foot obtained by these scanners, and the like, relate to static measurements, dynamic measurements, potentially in 2 directions of gait, dynamic measurement of pressure distribution, dynamic measurement of load rate, footprint size, automated risk analysis (and optionally corresponding insole advice), gait ratio graphs, foot movement references, foot angle analysis, exo-rotation angle, subtalar-joint flexibility, single-step foot timing, multi-step foot timing (step length, stride length, velocity), 3D measurements of the length of the foot, width of foot, arch height, arch length and/or circumferences.

In one embodiment the system of the invention is characterised in that the digital representation of a foot comprises or consists of one or more computer data files comprising information on foot length, foot width, 2D or 3D distribution of foot pressure and/or the external 3D shape of a foot, such as a 3D digital model of a foot, and/or a dynamic representation of the walking or running behavior of a user, such as pronation and/or supination. This information may also be referred to as "geometric characteristics of a foot or parts thereof". The generation and representation of such data falls within the abilities of one skilled in the art.

Various digital representations of geometric characteristics are described in the art. For example, the digital representations can be stored in a proprietary format, DXF format, XML format, or JPEG, BMP, TIF formates, or other format suitable for storing preferably 2D or 3D information on a user's body. In a preferred embodiment the scanned data enables analysis of the user's body or parts thereof via representation and/or analysis of cross section, slice area, surface area, and/or volume of the 3D data obtained. In particular, the analysis may be carried out by taking into account geometric characteristics of a user's feet or parts thereof.

Data export provides the opportunity to use the 2D or 3D-data in other design and/or manufacturing software. As such, the data may be incorporated into customized manufacturing units, such as those provided by Desma Schuhmaschinen GmbH, Germany, for example preferably automated devices for shoe production that are configurable according to the precise shape and other characteristics of a user's foot, preferably geometric characteristics of a user's foot. Examples of customized manufacture of shoes are provided below, for example in FIGS. 5-8, and relate in preferred embodiments to "multi-zone" injection molding of shoe soles or insoles.

In one embodiment the system of the invention is characterised in that the data communication and processing system comprises additionally a shoe database, wherein said shoe database comprises an electronic representation of one or more shoe models for customization from one or more providers. Preferably a matching and/or configurator engine is additionally present in the form of a computer-executable software (module) configured for virtual identification, customization and/or selection of a shoe from said shoe database for customization according to a digital representation of a foot of one or more users. In particular, the matching and/or configurator engine is configured to compare geometric characteristics of a foot or parts thereof and a digital representation of one or more shoes stored in the product database.

A further aspect of the invention relates to a computer-implemented method for selection of a shoe for customized manufacture, comprising:

providing geometric characteristics of a digital representation of the foot, or part thereof, of one or more users in a scan unit in the form of a computing device, said device being configured for storing and transmitting said representation, transmitting the geometric characteristics of said digital representation of a foot, or part thereof, to a user database comprised by a customized product selection platform, wherein said platform comprises
a) one or more computing devices,
b) a user database comprising geometric characteristics of a digital representation of a foot or part thereof of one or more users,
c) a product database comprising a digital representation of one or more shoes for customization from one or more providers,
d) a matching and/or configurator engine in the form of a computer-executable software configured for identification and selection, and optionally customization, of a shoe from said product database for customized manufacture according to geometric characteristics of a digital representation of a foot or part thereof of one or more users, and
e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit, and transmitting a product selection from said platform to a manufacturing unit of one or more providers, wherein said manufacturing unit is configured to manufacture a shoe in accordance with geometric characteristics of the digital representation of a foot or part thereof of a user wherein the matching and/or configurator engine is configured for a comparison of the geometric characteristics of the digital representation of a foot or part thereof of one or more users and the digital representation of one or more shoes stored in the product database.

In a preferred embodiment the method for customized shoe manufacture as described herein comprises generating a digital representation of a user's foot using a foot scanner configured for generating a 2D or 3D digital representation of a foot, such as a 2D flatbed scanner or pressure-sensing mat, or a 3D optical scanner for recovering the external 3D shape of a foot. In particular, it is preferred that the method for customized shoe manufacture comprises generating geometric characteristics of a digital representation of a user's foot using a foot scanner configured for generating geometric characteristics of a 2D or 3D digital representation of a foot.

The invention further relates to a method for customized shoe manufacture, wherein the data communication and processing system comprises additionally a shoe database, wherein said shoe database comprises an electronic representation of one or more shoe models for customization from one or more providers and a matching engine and/or a configurator engine in the form of a computer-executable software (module), wherein the user identifies, customizes and/or selects a shoe from said shoe database for customization according to geometric characteristics of a digital representation of a foot of one or more users.

In a preferred embodiment the system or method for customized shoe manufacture as described herein comprises manufacturing a shoe or part thereof in accordance with geometric characteristics of said digital representation.

Various technology is available to a skilled person, in addition to the injection/molding/pouring technology disclosed herein, that is suitable for manufacturing a shoe or part thereof in accordance with geometric characteristics of a digital representation of a foot or part thereof. For example, Desma Schuhmaschinen GmbH, Germany, supplies preferably automated devices for shoe production that are configurable according to the precise shape and other characteristics of a user's foot, preferably geometric characteristics of a user's foot.

Shoe soles are no longer considered to be single colored or single property objects formed from synthetic materials. Both aesthetic and technical developments have led to technologies for the manufacture of shoe soles or insoles with various hardness zones or colors. Furthermore, properties such as abrasion resistance, surface smoothness or chemical durability may be addressed by the following technology.

In a preferred embodiment the method or system for customized shoe manufacture as described herein is characterised in that the shoe manufacturing unit comprises an injection, molding and/or pouring device for the manufacture of a shoe, shoe sole and/or shoe in-sole.

In a preferred embodiment the method or system for customized shoe manufacture as described herein is characterised in that the injection, molding and/or pouring device comprises a mixing head capable of mixing multiple synthetic duroplastic and/or thermoplastic synthetic components (such as base materials and additives, which may be polymerizable and/or foamable) and distributing said components into a cavity in the form of a shoe sole or in-sole, whereby said shoe sole or in-sole comprises multiple areas comprising different components and/or mixtures of components with particular physical properties in accordance with said digital representation of the foot of a user, in particular geometric characteristics of said digital representation a user's foot.

In other words, in a preferred embodiment of the present invention, the shoe sole or in-sole comprises multiple areas comprising different components and/or mixtures of components with particular physical properties in accordance with geometric characteristics of said digital representation of the foot of a user. It may also be preferred that a form or a molding form is configured to provide a particular shape of the injected material.

In a preferred embodiment of the present invention, components of shoes, such as shoe soles or shoe insoles (which will be described herein by the single term "soles") may be manufactured in accordance with geometric characteristics of said digital representation of a foot or part thereof of a user according to the technology described herein.

For example, a shoe sole can be divided into multiple sectors, for example three sectors, in particular a heel sector, a middle foot sector and a foot tip or toe sector. These various sectors may be formed with various colors or densities in order to provide a customized shoe sole.

In one embodiment, different materials comprising various synthetic materials or additives duroplastic and/or thermoplastic synthetic components (such as base materials and additives, which may be polymerizable and/or foamable) may be poured and/or injected in a particular order through a mixing head, thereby injecting the various components or mixtures thereof into distinct sectors. Multiple components may be provided into the mixing head, where they are subsequently mixed to provide a homogenous or semi-homogenous solution, before being injected or poured in a controlled order into the form cavity of the shoe sole. Optionally, a form or molding form may be applied to the injected material in order to provide a particular shape.

This technology is available either as injection or pouring technology. For example, the mixing head may be arranged in a horizontal position to the sole form, into which the synthetic material is injected or poured.

In a pouring method the mixing head may be positioned in a vertical position over the open cavity in the form of a shoe sole and may be led in a particular route or shape over the cavity in order to distribute the various synthetic materials for each sector into the form of the shoe sole.

Through such methods a shoe sole may be produced with individual sectors with different colors, material densities, abrasion properties, hardness, flexibility, depending on the synthetic material used for production.

Figure 5:
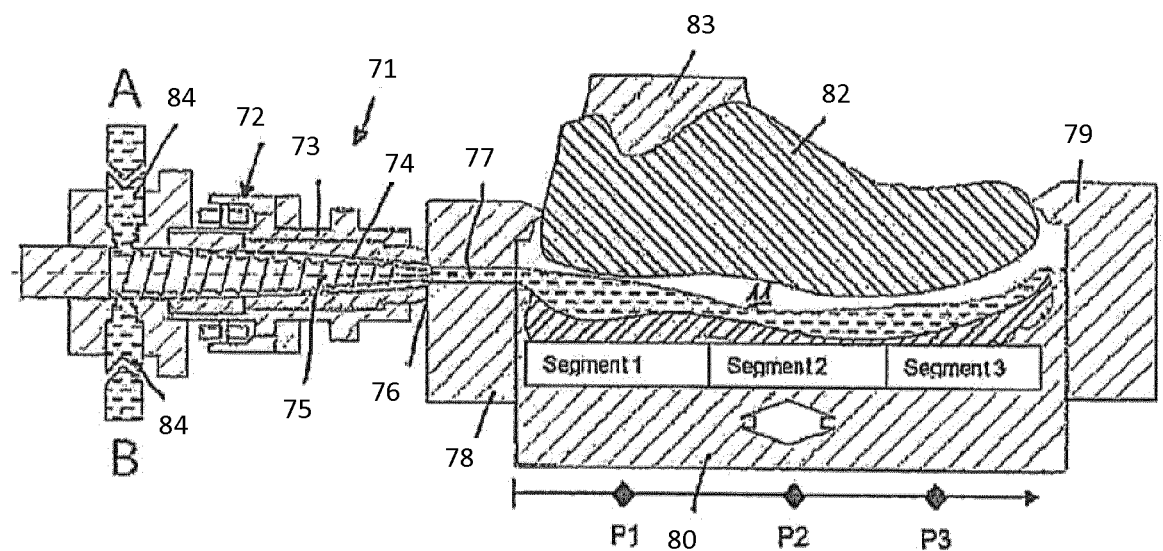
Figure 6:
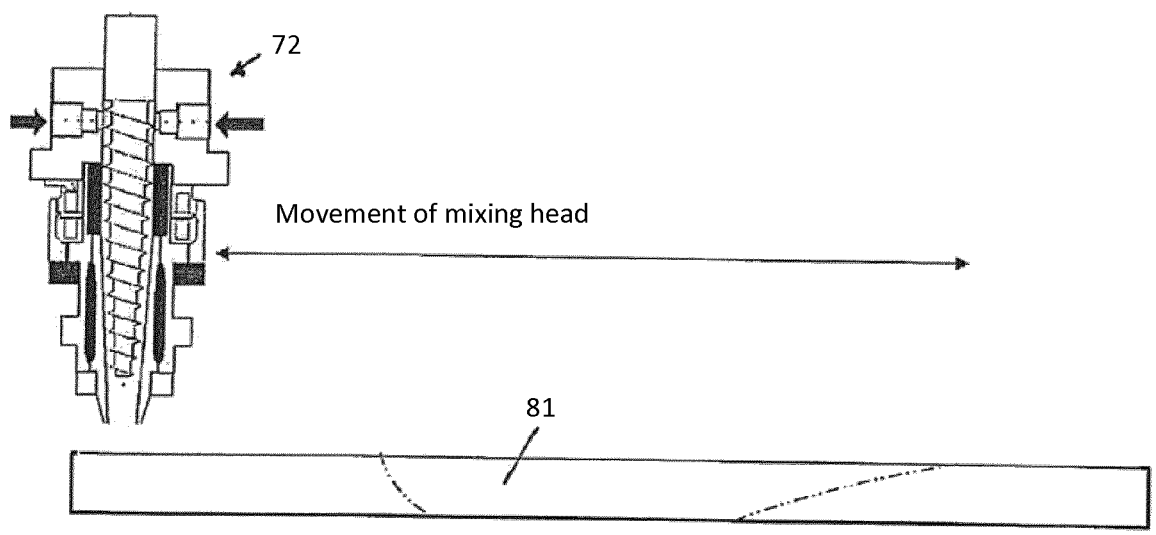

A preferred synthetic material for the shoe sole manufacturing process is polyurethane. The present invention incorporates technology where the liquid components for polyurethane production, optionally with additives, are mixed and then injected and/or poured into the different zones of the shoe sole. The FIGS. 5 and 6 provided herein demonstrate a mixing head in which polyurethane is used as a preferred synthetic material, wherein any duroplastic material or elastomer may be used, most preferably polyurethanes, TPU and rubber. Both solid polyurethane and/or foamed polyurethane may be employed. Both options can be used for the manufacture or custom-made soles according to the present invention by using the injection and/or pouring of the additives into the multizone shoe soles.

Preferred materials therefore relate to duroplastic or elastomeric synthetic materials, such as but not limited to solid or foamed polyurethane, thermoplastic elastomers (TPE), sometimes referred to as thermoplastic rubbers, such as thermoplastic polyurethanes (TPU), thermoplastic co-polyester or thermoplastic polyamides.

In order to produce such shoe soles a commonly available mixing head may be applied, which is preferably assembled with a rotating extruder screw, whereby the extruder screw ends in a nozzle from which the synthetic material is injected and/or poured into the shoe sole form cavity. The synthetic material may be added to the screw with any given additives, mixed and subsequently excluded into the cavity. Various channels may be present for introducing multiple, potentially different, synthetic materials with or without various additives into the extruder screw via multiple valves. Various valves could be attached to mixing head with an appropriate control program, thereby allowing precise control of which material is injected and/or poured into which shoe sole sector. A software is capable of controlling the valves in order to regulate which valve opening corresponding to the various synthetic materials is applied to the extruder.

The shoe sole form cavity is preferably prepared from two shaped side elements and a stamping element, whereby the side elements may be attached to each other before filling or injecting and before the stamping element, or a base element is used to compress the cavity volume in order to press the material into the appropriate form. For example, the cavity may be closed from above using a shoe upper or model of a foot enclosed by a shoe upper. The cavity may be closed from below with a base element underneath the shoe sole. In a preferred embodiment the shoe upper may be bound to the sole by pressing the stamping element surrounded by the shoe upper into the shoe sole form cavity after the synthetic shoe sole has been injected and/or poured.

In a preferred embodiment a mobile rack or device is envisaged for each additive or each synthetic material. Each of these racks or devices preferably comprises a pump, gas tank and a computer controller for dosing the various components into the valves of the mixing head. Such racks or devices may be positioned on wheels and positioned appropriately in order to allow effective production.

Through the precise and quick dosing of various synthetic materials into the screw component of the mixing head precise structures and functions in the shoe sole possible, for example a strict and clear separation between sectors may be obtained order to allow manufacture of a shoe sole in accordance with the digital representation of the foot of a user, in particular in accordance with geometric characteristics of the digital representation of the foot of a user.

Embodiments Relating to Full Body Scanning for Wearable and/or Medical Products

In one embodiment of the invention the scan unit is a body scan unit configured for generating a 2D or 3D digital representation of essentially the entire body of a user, such as a 3D optical scanner for recovering the external 3D shape of the user's body.

Currently a number of systems are available to capture essentially human body avatars, extract precise body measurements, and securely store and aggregate and process that data for the purpose of data dissemination in computer processors and via the internet. There are a number of existing body scanning systems. For example, Human Solutions, TC-2 (NX-16 and KX-16), Vitus (Smart XXL), Styku (MeasureMe), BodyMetrics and Me-Ality are examples of existing body scanning systems suitable for application in the present invention. These systems relate primarily to body scanners where the user stands still in a spread pose and the system then create body contour maps based on depth sensors, white light projectors and cameras, or lasers. These systems then use those body contour maps (avatars) to extract measurements about the user.

Alternative body scanning and measurement systems are suitable for application in the present invention such as systems and methods to capture and process body measurement data including one or more body scanners, each body scanner configured to capture a plurality depth images of a user, such as described in US 20140340479. Furthermore, scanning technology as described by the Cornell University 3D Body Scanner project (Ashdown, Loker, Mete).

In preferred embodiments the software application can collect, generate and/or display body scan data in multiple formats suitable for the present invention, for example using points, a triangulated wireframe, a wireframe with surface rendering, or simply as a smooth surface. One example of this software is the Polyworks software, as described under the Cornell University 3D Body Scanner project. Additionally, slices can be taken at any orientation, enabling the measurement of circumferences and view cross sections in different areas of the body. Even for bodies with similar circumference measures, variation in shape can factor into garment fit.

Also applicable are those systems described by Human Solutions (DITUS MC for full body scans, VITUS AHEAD for head scans suitable for designing glasses, hats or helmets, FOOTIN 3D for foot scans), or methods for 3D shape and size measurement of a 3D body surface comprising providing a 3D scanner as described in U.S. Pat. No. 6,968,075.

For example, the DITUS MC from Human Solutions enables the precise taking of measurements and three-dimensional imaging of the human body, high level of customer comfort thanks to short scan times and instant results, a high degree of mobility due to low weight and easy assembly, instant capture of 50 dimensions, a measurement duration: less than 1 sec, based on a measurement principle of optical triangulation and infrared, with the number of sensors being 12 (Xtion PRO LIVE), a scanning volume: 2100 mm (H) 900 mm (L), 900 mm (B), depth resolution: 5 mm (typical), scanner dimensions (assembled): 1850 mm (H), 2200 mm (L), 2400 mm (B), total weight: 30 kg, and export formats of PLY, OBJ, STL, ASCII, DXF.

Embodiments related to full body scanning may be applied in preferred embodiments in the manufacture of apparel in accordance with the scanned data. It is preferred that the scanned data comprises geometric characteristics of the digital representation of a body or part thereof. In one embodiment a system as described herein is provided, wherein, by way of non-limiting example, the manufacturing unit is a computer controlled machinery for the cutting, sewing, and other processes involved in the fabrication of a custom fitted article of clothing for the customer whose body measurements were the input controlling the operation of the machinery, as described in U.S. Pat. No. 5,956,525.

Embodiments Relating to the Head

In a preferred embodiment the present invention relates to a system as described herein, wherein said wearable and/or medical product is customized to the users head.

In a preferred embodiment the present invention relates to a system for customized hat, helmet or other headgear manufacture, comprising:
  a scan unit configured for storing and transferring a digital representation of a head or part thereof of one or more users,
  a hat, helmet or other headgear manufacturing unit of one or more providers, wherein said manufacturing unit is configured to manufacture a hat, helmet or other headgear or part thereof in accordance with geometric characteristics of said digital representation, and
  A customized product selection platform comprising
    a) one or more computing devices,
    b) a user database comprising a digital representation of a head or part thereof of one or more users,
    c) a product database comprising a digital representation of one or more products for customization from one or more providers,
    d) a matching and/or configurator engine in the form of a computer-executable software configured for identification and selection, and optionally customization, of said product from said product database for customized manufacture according to a digital representation of a head or part thereof of one or more users, and
    e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit wherein the matching and/or configurator engine is configured for a comparison of geometric characteristics of the digital representation of a head or part thereof of one or more users and the digital representation of one or more products stored in the product database.

Devices for head scanning are known to one skilled in the art.

In one embodiment the system as described herein is characterized in that the scan unit is a head scan unit configured for generating a 2D or 3D digital representation of the head of a user, such as a 3D optical scanner for recovering the external 3D shape of the user's head. In one embodiment the system as described herein is characterized in that the scan unit comprises a scanning device configured for generating a 2D or 3D digital representation of the head.

The invention therefore relates to a system as described herein for customizing a product according to the head of a user, wherein, by way of non-limiting example, the scan unit is a 3D optical scanner reading of the head shape as described in WO1997040716. In this implementation, the statement of the shape of the wearer's head is a digital reading without contact, for example, a two-dimensional digital reading obtained by a 3D scanner scanning profiles formed by a laser beam plane. Alternatively, US20060101559 describes suitable scanning equipment to generate a computer-readable data file of a surface map of the headform (i.e. digitizing the headform). This data file is then used to direct CNC machinery, or other computer controlled milling device or tool, to machine a pre-made energy-absorbing liner "blank" so as to provide an inner surface thereof having a complementary contour to the wearer's head. In a further embodiment also described below, the scanning equipment can scan the wearer's head directly to generate the computer-readable data in the manufacture of a custom-fitted liner.

Manufacturing units for producing a customized hat, helmet or other headgear are known to a skilled person.

The invention therefore relates to a system as described herein for customizing a product according to the head of a user, wherein, by way of non-limiting example, the manufacturing unit is a numerically controlled machine for manufacturing custom liners for helmets as described in WO1997040716. The liner may also be made from a block of foam, by cutting using a numerically controlled machine operator scanning above, then a jacket terms of comfort and finishing. After manufacture the custom liner is placed in a standard helmet. Such a helmet manufacturing method allows the realization of an integrated visual helmet adapted bearer without the addition of a mechanical visual adjustment. It makes it possible to separate in time and space the two main steps of embodiments constituted on the one hand the shape of the pointed head and on the other hand the embodiment of the custom liner. US20060101559 provides another non-limiting example of a method for making a custom-fitted helmets based on computer-readable scanning data of the customer's head.

Embodiments Relating to the Ear/Hearing Aids

In a preferred embodiment the present invention relates to a system as described herein, wherein said wearable and/or medical product is customized to the user's ear(s).

In a preferred embodiment the present invention relates to a system for customized hearing aid, ear plug or other ear mold or ear product manufacture, comprising:
- a scan unit configured for storing and transferring a digital representation of an ear or part thereof of one or more users,
- a hearing aid or ear plug manufacturing unit of one or more providers, wherein said manufacturing unit is configured to manufacture hearing aid, ear plug or other ear mold or ear product or part thereof in accordance with geometric characteristics of said digital representation, and
- A customized product selection platform comprising
  - a) one or more computing devices,
  - b) a user database comprising a digital representation of an ear or part thereof of one or more users,
  - c) a product database comprising a digital representation of one or more products for customization from one or more providers,
  - d) a matching and/or configurator engine in the form of a computer-executable software configured for identification and selection, and optionally customization, of said product from said product database for customized manufacture according to a digital representation of an ear or part thereof of one or more users, and
  - e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit wherein the matching and/or configurator engine is configured for a comparison of geometric characteristics of the digital representation of an ear or part thereof of one or more users and the digital representation of one or more products stored in the product database.

Devices for ear scanning are known to one skilled in the art.

The invention therefore relates to a system as described herein for customizing a product according to the ear(s) of a user, wherein, by way of non-limiting example, the scan unit is an ear scan unit for generating a three dimensional representation of an ear canal. Such devices have been described for example in US20070127756 using optical coherence tomography (OCT). Cross-section images of an ear canal are taken by, for example, rotating an OCT imaging sensor about a predetermined axis at each of a plurality of positions. In accordance with another embodiment, a contour line is then identified in each of the cross section images and a flow algorithm is used to identify the boundary of the ear canal cross section. Once the boundaries of each cross section have been identified, all of the cross section images are combined to generate a three dimensional image of the ear canal. US20050088435, as a non-limiting example, describes a miniature 3D camera hardware design is provided for image acquisition, and software algorithms are provided to compute a digital model of the internal ear and ear canal.

Manufacturing units for producing a customized hearing aid, ear plug or other ear mold or ear product are known to a skilled person.

The invention therefore relates to a system as described herein for customizing a product according to the ear(s) of a user, wherein, by way of non-limiting example, the manufacturing unit is a numerically controlled machine for manufacturing hearing aids that is automatically operated based on the obtained numerical data of the three-dimensional structure of the ear canal and automatically forms the outer shell part of the hearing aid. Such machines have been described in U.S. Pat. No. 5,056,204.

Embodiments Relating to the Hand/Gloves

In a preferred embodiment the present invention relates to a system as described herein, wherein said wearable and/or medical product is customized to the user's hand(s).

In a preferred embodiment the present invention relates to a system for customized glove manufacture, comprising:
- a scan unit configured for storing and transferring a digital representation of an hand or part thereof of one or more users,
- a glove manufacturing unit of one or more providers, wherein said manufacturing unit is configured to manufacture a glove or part thereof in accordance with geometric characteristics of said digital representation, and
- A customized product selection platform comprising
  - a) one or more computing devices,
  - b) a user database comprising a digital representation of a hand or part thereof of one or more users,
  - c) a product database comprising a digital representation of one or more products for customization from one or more providers,
  - d) a matching and/or configurator engine in the form of a computer-executable software configured for identification and selection, and optionally customization, of said product from said product database for customized manufacture according to a digital representation of a hand or part thereof of one or more users, and
  - e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit, wherein the matching and/or configurator engine is configured for a comparison of geometric characteristics of the digital representation of a hand or part thereof of one or more users and the digital representation of one or more products stored in the product database.

Devices for hand scanning are known to one skilled in the art.

The invention therefore relates to a system as described herein for customizing a product according to the hand(s) of a user, wherein, by way of non-limiting example, the scan unit is a scanner for customization of gloves, wherein the scanner for the customization of the gloves can accurately describe the outline and the characteristics of the hands of users so as to determine the gloves ordered by the users, and thus comfortableness and attractiveness are achieved in wearing. U.S. Pat. No. 8,512,615 describes a scanning unit or imaging system generating data-sets describing the three-dimensional form or the user's hand.

Manufacturing units for producing a customized glove are known to a skilled person.

The invention therefore relates to a system as described herein for customizing a product according to the hand(s) of a user, wherein, by way of non-limiting example, the manufacturing unit is a system for making custom-fit surgical gloves that is taking a data-set describing the three-dimensional image of the users hand, the three-dimensional image providing data on the dimensions of the users hand, using the data to make a mold of the users hand based on the data from the three-dimensional image, and using the mold of the users hand to prepare a former for use in making the custom-fit surgical glove. Such a system has been described by U.S. Pat. No. 8,512,615.

Embodiments Relating to Eyes/Spectacles

In a preferred embodiment the present invention relates to a system as described herein, wherein said wearable and/or medical product is customized to the user's eye(s), nose, forehead or head.

In a preferred embodiment the present invention relates to a system for customized spectacles or glasses manufacture, comprising:
  a scan unit configured for storing and transferring a digital representation of an eye(s), forehead or head or part thereof of one or more users,
  a spectacles manufacturing unit of one or more providers, wherein said manufacturing unit is configured to manufacture the frame or other component of spectacles or part thereof in accordance with geometric characteristics of said digital representation, and
  A customized product selection platform comprising
    a) one or more computing devices,
    b) a user database comprising a digital representation of an eye, nose, forehead, head or part thereof of one or more users,
    c) a product database comprising a digital representation of one or more products for customization from one or more providers,
    d) a matching and/or configurator engine in the form of a computer-executable software configured for identification and selection, and optionally customization, of said product from said product database for customized manufacture according to a digital representation of an eye, nose, forehead, head or part thereof of one or more users, and
    e) data connections enabling transfer of data between (i) said scan unit and said user database, (ii) said user database and said matching and/or configurator engine, (iii) said product database and said matching and/or configurator engine, and (iv) said matching and/or configurator engine and said manufacturing unit,
wherein the matching and/or configurator engine is configured for a comparison of geometric characteristics of the digital representation of an eye, nose, forehead, head or part thereof of one or more users and the digital representation of one or more products stored in the product database.

Devices for eye, nose, forehead or head scanning are known to one skilled in the art.

The invention therefore relates to a system as described herein for customizing a product according to the eye(s), forehead or head of a user, wherein, by way of non-limiting example, the scan unit is configured for scanning at least a part of a customer's face. Such a system has been described by US2015061166. The scanning unit comprises an eye scanner for scanning the customer's eyes in order to determine the visual capacity of the customer's eyes. The eye scanner comprises e.g. a refractometer, optometer and/or an ophthalmoscope (objective determination method). The determined parameters regarding the visual capacity of the customer are hereinafter referred to as visual capacity parameters.

Alternatively or additionally, the scanning unit comprises a 3D scanner, e.g. a laser scanner or a scanner with multiple optical CCD (Charged-Coupled Device) cameras, for determining the three-dimensional shape of the customer's face or even the pro-file of the whole customer's head. The knowledge of the individual shape of the customer's face advantageously allows to perfectly adapt the form of the spectacle to the customer's face. In this way, the wearing comfort for the customer can be increased significantly. The parameters determined by the scanning unit are hereinafter referred to as scanning parameters. According to another preferred embodiment of the present invention, the device comprises a graphical user interface. It is herewith advantageously possible that the customer selects a certain base frame, which preferably has already been adapted to the shape of the customer's face, and subsequently freely modifies the design of the base frame to his individual requests and requirements. For example, the color, the pattern, the shape, the thickness of the frame is freely configured by the customer. Suchlike individually configurable parameters are referred to as customer parameters. In particular, the user interface comprises a display and preferably a touch pad which displays the actual design of the spectacle.

Manufacturing units for producing a customized spectacle frame or lenses are known to a skilled person.

The invention therefore relates to a system as described herein for customizing a product according to the eye(s), forehead or head of a user, wherein, by way of non-limiting example, the manufacturing unit is a system for producing custom-made spectacles comprising at least a printing device for printing a spectacle lens and/or a spectacle frame, wherein the printing device is configured for printing the spectacle lens and/or the spectacle frame in dependency of scanning data of the scanning unit. Such printing devices have been described by US2015061166 in detail.

A further aspect of the invention relates to a system for personalized wearable and/or medical product selection, comprising:
  a scan unit configured for storing and transferring a digital representation of a body or part thereof of one or more users,
  a provider unit of one or more providers, wherein said provider unit is configured to manufacture, personalize and/or store a wearable and/or medical product or part thereof in accordance with geometric characteristics of said digital representation, and
  A customized product selection platform comprising
    a) one or more computing devices,
    b) a user database comprising a digital representation of a body or part thereof of one or more users,
    c) a product database comprising a digital representation of one or more products for customization from one or more providers,
    d) a matching and/or configurator engine in the form of a computer-executable software configured for identification and selection, and optionally customization, of said product from said product database, and
    e) data connections enabling transfer of data between (i) said scan unit and said user database, (ii) said user database and said matching and/or configurator engine, (iii) said product database and said matching and/or configurator engine, and (iv) said matching and/or configurator engine and said provider unit,
wherein the matching and/or configurator engine is configured for a comparison of geometric characteristics of the digital representation of a body or part thereof of one or more users and the digital representation of one or more products stored in the product database.

In such an embodiment the selection of a product that fits to the best fit model is encompassed, preferably in combination with a customization of the product according to the methods and systems above for customized manufacture of such a product.

The present invention, in preferred embodiments, comprises one or more, in any given combination, of the software modules described below in the context of the figures and/or examples. A skilled person is aware that particular details of the software modules may be extrapolated and integrated into the concepts of the invention as described above.

FIGURES

The invention is demonstrated by way of the example by the examples and figures disclosed herein. The figures provided represent particular embodiments of the invention and are not intended to limit the scope of the invention. The figures are to be considered as providing a further description of possible and potentially preferred embodiments that enhance the technical support of one or more non-limiting embodiments.

FIG. 1: Schematic representation of a preferred embodiment of the system of the present invention, demonstrating one or more users 60 (n represents any number of), who pass body information to a scanning device 61. Data obtained from said scanning device 61 is transmitted to a scan unit 51, and from the scan unit 51 said data is transmitted to a user database 56. The body data is preferably maintained for each user 60 in a user profile 56 within said user database 56. The data from the user database 56 is transmitted to a matching and/or configurator engine 59, which also receives data from a product database 57, comprising product profiles 67, in which a particular product is represented digitally 58. The matching and/or configurator engine 59, performing its function as described herein, transmits data to a manufacturing unit 53 of a provider 54. The provider 54 also transmits data on products 50 to the product database 57 for utilization by the matching and/or configurator engine 59. The manufacturing unit 53 executes manufacture of the customized product 50 in accordance with geometric characteristics of the digital representation of the body or part thereof 62 of the user 60, wherein said product 50 is sent to the user 60.

Figure 2:
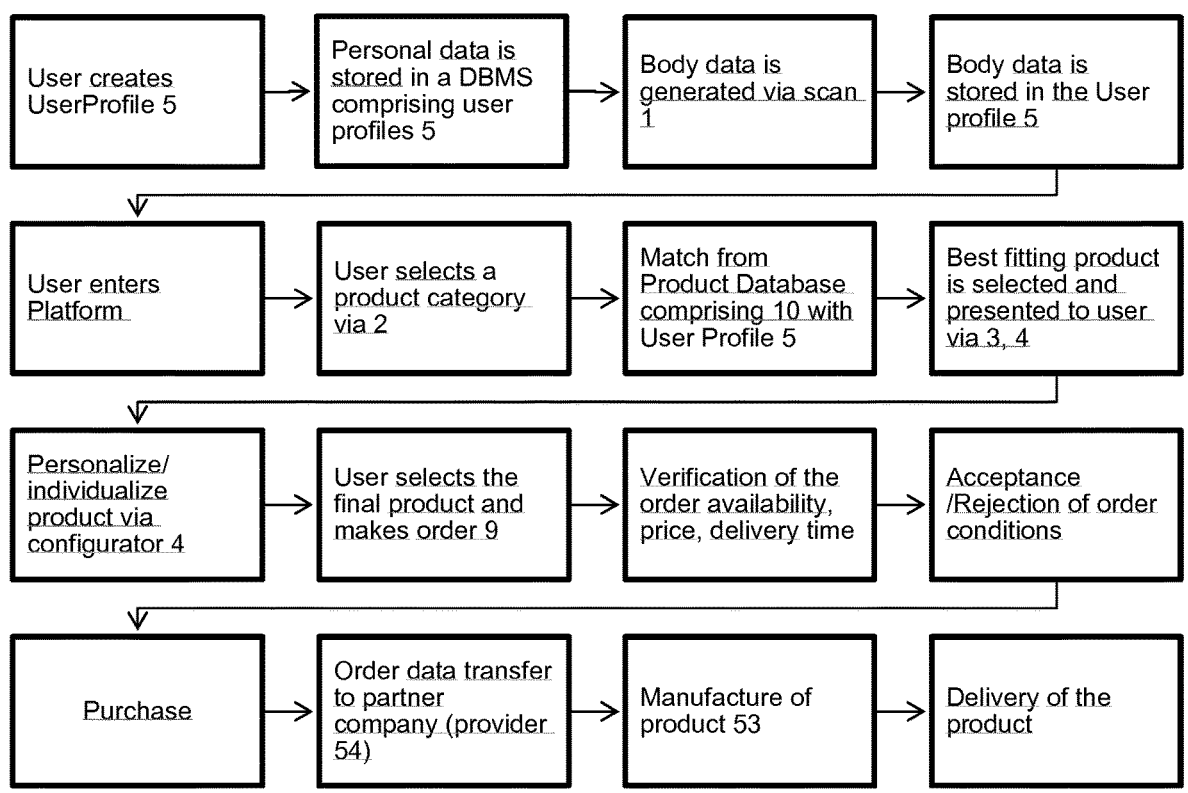

FIG. 2: Preferred sequential representation of the process encompassed by the system and method of the present invention. FIG. 2 describes creation of a user profile 5 and subsequent storage of the user data in user database 56 (DBMS). Body data, preferably a digital representation of a body or part thereof 52 of a user 60, is generated and/or stored via a scan unit 51, scanning device 61 and/or the scan software module 1. In the context of the present invention, it is preferred that the body data and/or the digital representation comprise geometric characteristics of a body or part thereof 52 of a user 60. The body data is stored in the user profile 5. After entering the customized product selection platform 55 a user selects a product category via sales tools 2 and a match is obtained between the data from the user profile 5 and the product database 57 comprising one or more digital representations of one or more products 58. A product 50 is selected for manufacture and presented to the user via the Matching and/or configurator engine 59, preferably comprising the Sales Match 3 software module. Particular products 50 may be presented to the user based on the analytics 14 and/or prediction modules 15. The selected product 50 may be individualized and/or customized via the matching and/or configurator engine 59 preferably comprising the Configurator 4 software module. The user 60 selects a product and makes an order using the order 9 software module. Ordering verification is conducted and purchase completed. The order data is transferred to the provider 54 comprising a manufacturing unit 53, manufacture is conducted and the product 50 is delivered. Data and/or product transmission and/or data connections between various modules are shown as arrows.

Figure 3:
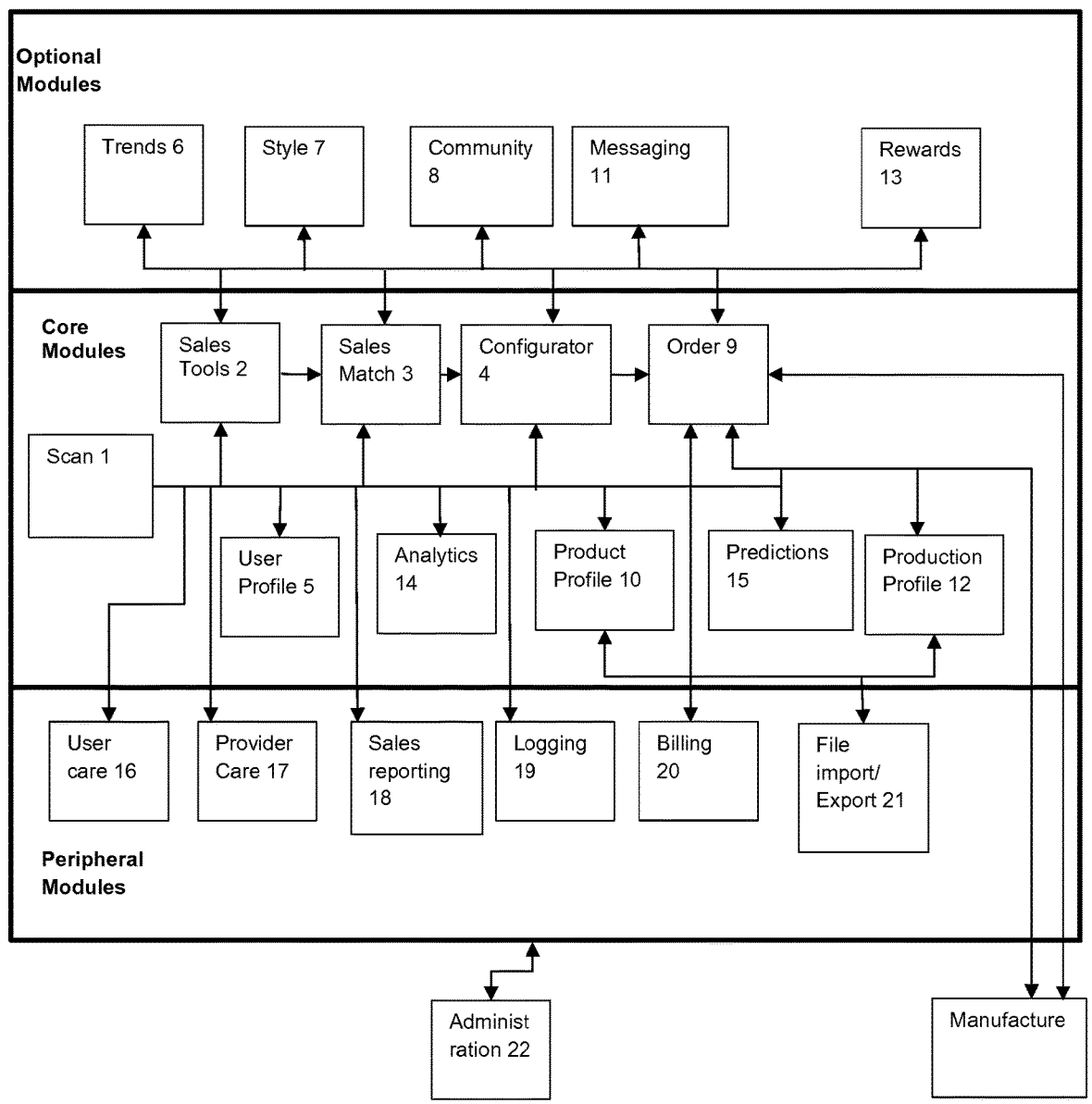

FIG. 3: Preferred representation of the system structure of the modules, such as may be found in the matching and/or configuration engine 59. Shown as core modules are Scan 1, Sales Tools 2, Sales Match 3, Configurator 4, User Profile 5, Ordering 9, Product Profile 10, and Production Profile 12. Shown as further optional core modules are Trending 6, Style 7, Community 8, Messaging 11, Rewards 13, Analytics 14 and Predictions 15. Shown as peripheral modules are User Care 16, Provider Care 17, Sales Reporting 18, Logging 19, Billing 20, File Import/Export 21 and Administration 22. Data and/or product transmission and/or data connections between various modules are shown as arrows. Additional data connections are shown in Table 2.

Figure 4:
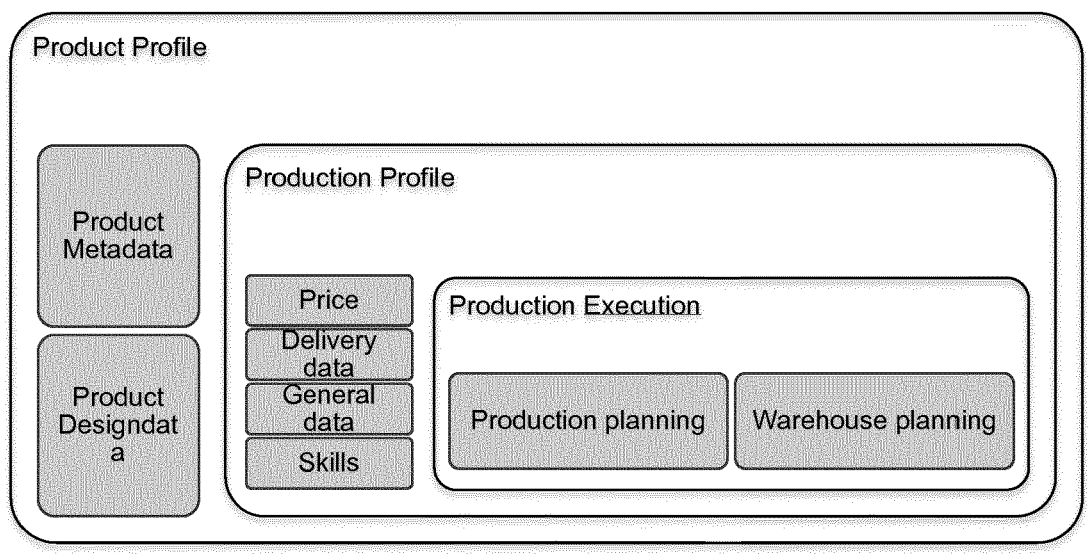

FIG. 4: Schematic representation of the subdivision of the production profile and data comprised therein.

FIG. 5: Longitudinal section of a molding device for the manufacture of a shoe sole and injection unit.

FIG. 6: The side cross-section of a casting mold with vertically arranged above casting unit.

Figure 7:
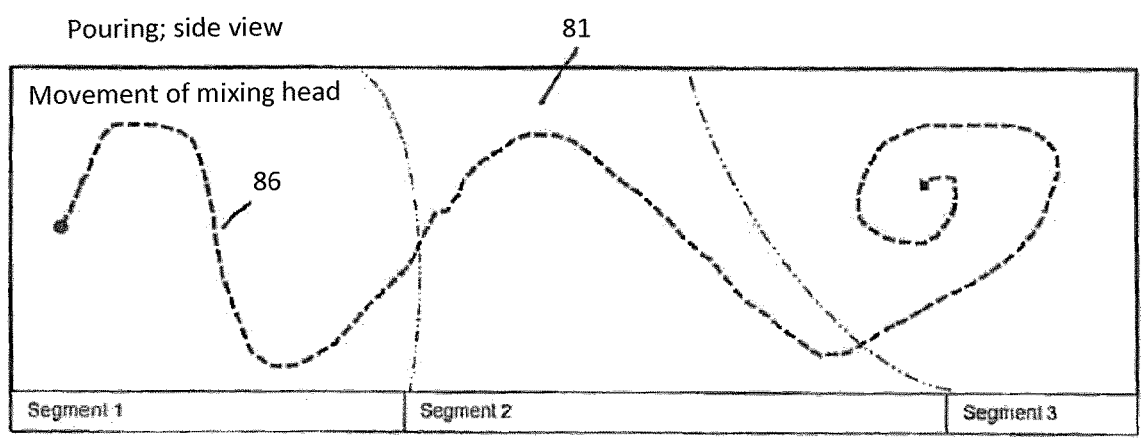

FIG. 7: Casting mold in plan view.

Figure 8:
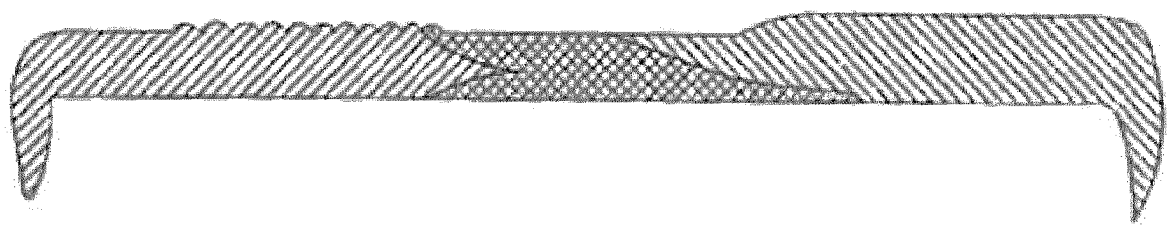
Figure 8:
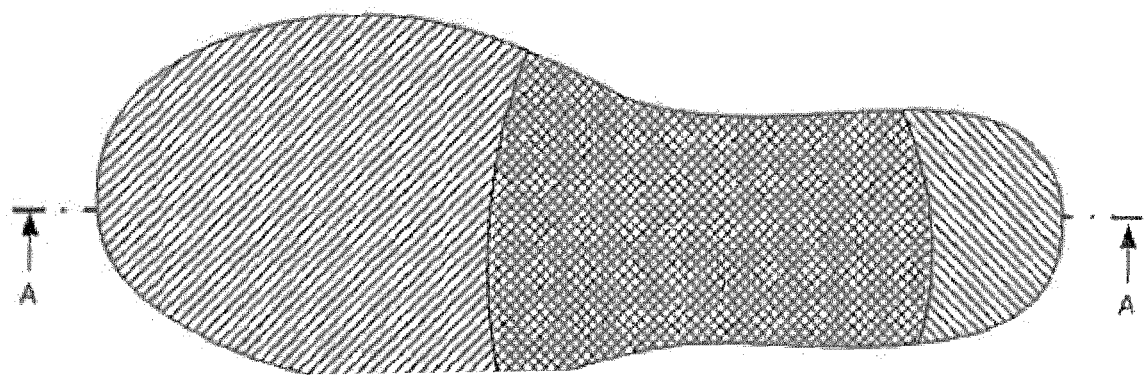
Figure 8:
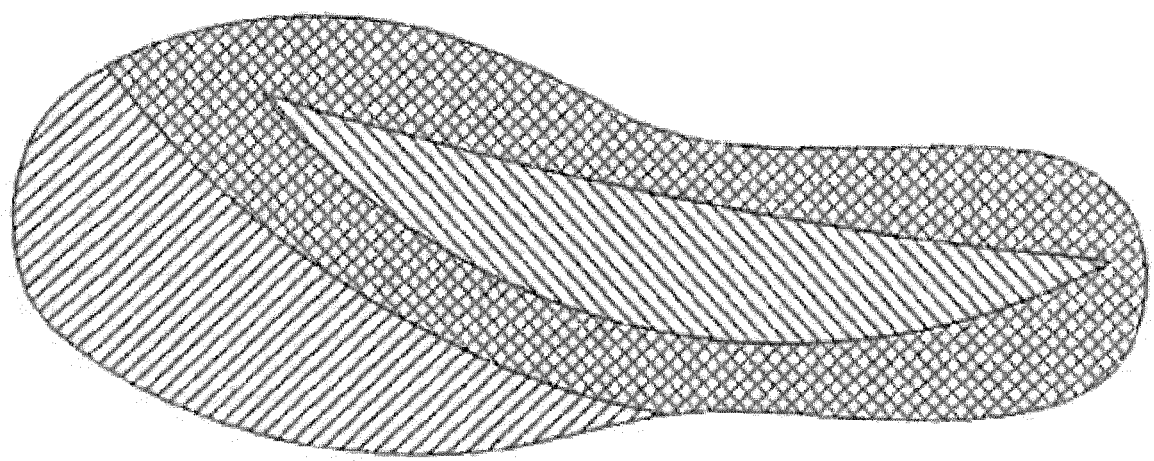

FIG. 8: Soles with sectors of different properties.

Figure 9:
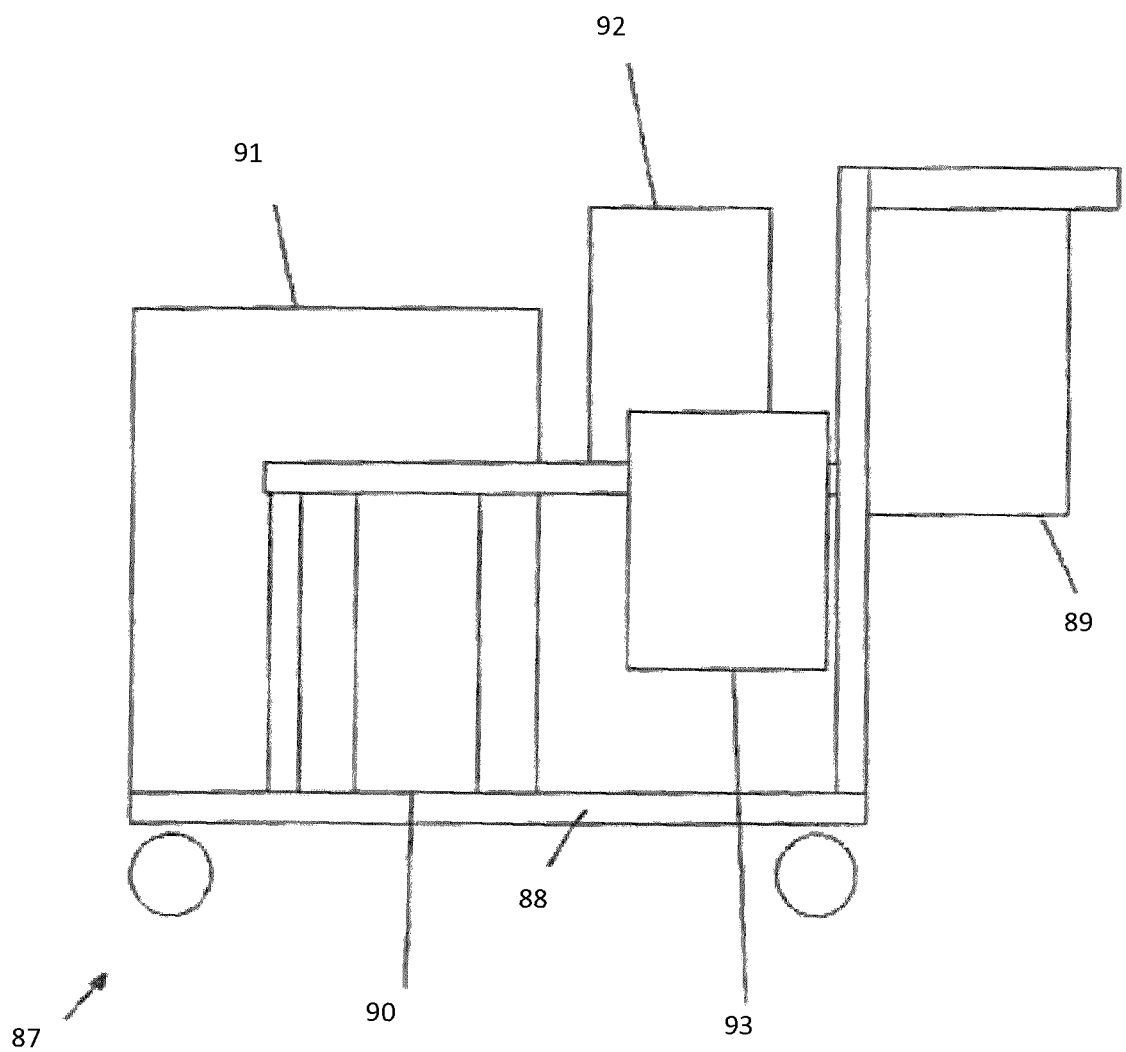

FIG. 9: Schematic representation of an additive cart.

Figure 10:
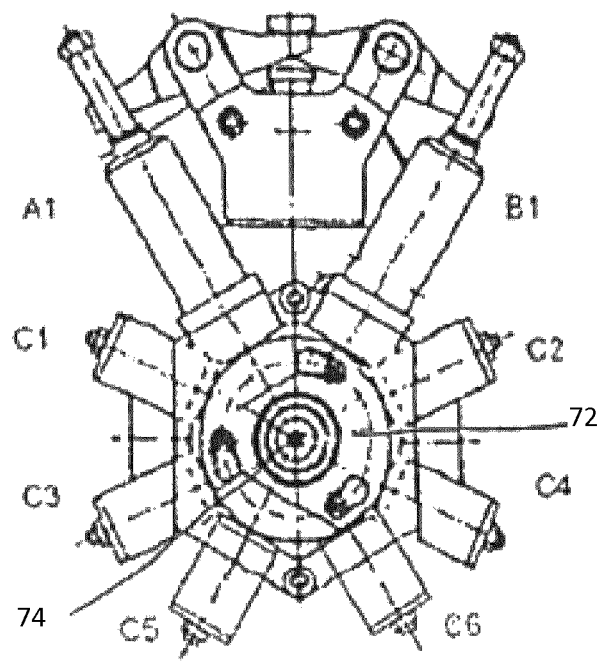

FIG. 10: Valve assembly.

Figure 11:
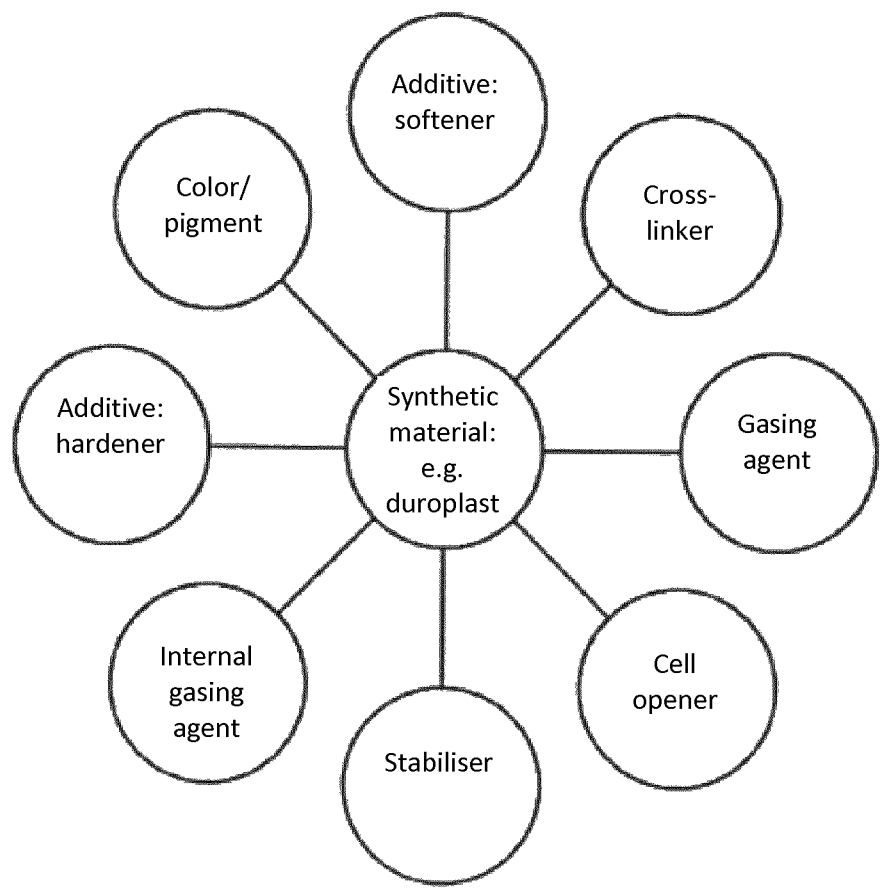

FIG. 11: Diagram of additives.

The following reference signs are used in the figures:

Scan (1)
Sales Tools (2)
Sales Match (3)
Configurator (4)
User Profile (5)
Trending (6)
Style (7)
Community (8)
Ordering (9)
Product Profile (10)
Messaging (11)
Production Profile (12)
Rewards (13)
Analytics (14)
Predictions (15)
User Care (16)
Provider Care (17)
Sales Reporting (18)
Logging (19)
Billing (20)
File Import/Export (21)
Administration (22)
Wearable and/or medical product (50)
Scan unit (51)
Digital representation of a body or part thereof (52)
Manufacturing unit (53)
Providers (54)
Customized product selection platform (55)
User database (56)
Product database (57)
Digital representation of one or more products (58)
Matching and/or configurator engine (59)
User (60)

-continued

Scanning device (61)
Shoe or part thereof (62)
Digital representation of a foot or part thereof (63)
Shoe manufacturing unit (64)
Digital representation of one or more shoes (65)
Injection and/or molding device (66)
Sole (71)
mixing head (72)
housing (73)
tapered screw/screw chamber (74)
mixing screw (75)
nozzle mouthpiece (76)
sprue runner (77)
molding tool (78)
two side molding elements (79)
base stamp (80)
cavity (81)
shoe upper (82)
block (83)
supply channels (84)
track or route (86)
reference (87)
frame (88)
electric control (89)
metering pump (90),
temperature-controlled pressure vessel (91)
temperature control unit (92)
hose (93)

EXAMPLE

The invention is demonstrated by way of the examples disclosed herein. The examples provide technical support for and a more detailed description of potentially preferred, non-limiting embodiments of the invention.

System Overview:

Described herein is a brand- and provider-independent web-based platform where individual user profiles can be created. Within these user profiles, different kinds of digitalized body data from a verified user can be stored, which will then be used for a specific selection of products, such as textiles, shoes, pants, shirts, gloves hats and so forth. The saved body data will be used to offer a much more precise selection of personal items for the consumer.

Based on the specific user behavior during the customer journey, a "Big Data Analytics" can be applied to offer a much more precise product to the consumer. This principle assumes an accurate evaluation of the available data. To be as close to the user profile as possible, it is advantageous if sufficient profile data has been collected from the user. The recording of the consumer data is compliant to existing national and international Privacy Policies. Secure data handling is assured.

The necessary personally identifiable data can be entered into the platform from all connected devices, such as from home, in stores, mobile devices, and so forth. This data is then stored in a secured Database Management System (DBMS). The physical/technical accessibility of the DBMS is available worldwide. A corresponding redundancy of the system to ensure the proper functioning can be established. When the respective personal User profiles are stored in the DBMS, selected Partner companies (providers) must be connected to this database in order to offer their customizable products and accept orders from the users.

If a certain product branch has been selected, such as medical or wearable, or shoes, textiles, headgear, gloves, jewelry, glasses, hearing aids/ear plugs, all products from the partner companies are offered to the consumer via a product database and configurator. After the consumer has made a more precise and concrete product selection, an individual product offer can be submitted to the consumer.

This product offer can then be idealized and adjusted according the user profile, by the means of a better fitting of the product or a closer accordance of the style from the individual consumer. The improved fitting of the product is in particular achieved by using geometric characteristics of a body or parts thereof of a user or their digital representation. Corresponding user preferences are taken into account as well as the physical and/or geometric requirements. Out of that selection, the best optimized product for the consumer is identified. The selection can contain one or more products out of the product category.

One of the most advantageous functions within the system of the present invention is the possibility to individualize the product according to the specific needs of the consumer, for example geometric characteristics of his body or parts thereof. To allow this, the partner company (provider) classifies specific products in the product database according to certain characteristics, such as min/max customizable dimensions or performance data, which is potentially individualized by the consumer.

A preferred series of steps encompassed by the system or method of the invention is as follows:

User creates a user profile (later profile extension possible)

Storage of the Profile in the DBMS

User enters a computer interface of the system via any given operating or computing device, via e. g. PC, Tablet, Smartphone or Terminal Selection of the product category, e.g. shoes Input/Selection of the shoe type, e.g sports shoe The system of the invention then selects one or more potentially best fitting products, by using the available user body data from of the user profile and comparing it with characteristics, such as min/max customizable sizes, shapes, colors, forms, textures, materials, and so forth, of the product stored in the product database, whereby additional trending, analytics and/or prediction data may be assessed and considered during selection.

The system provides the one or more products as a selected product from the contracted partner (provider) including customization options with respect to the product characteristics.

The consumer is able to select the offered products or can individualize the offered products by the means of style or performance in a configuration engine.

Settlement of payment arrangements.

Order will be send to the contract partner company (provider) for manufacture.

After production of the product the product will be sent to the consumer

In addition, the system comprises the possibility to use mobile tracking in order to offer the consumer, if wanted, personalized products in geographical proximity to the actual position of the consumer. If the consumer wants to use the mobile tracking functionality, there is an automated routing of the consumer to the next shopping point where the selling opportunity is located.

The system as described herein is equipped with the possibility for push notification functionality at Smartphones or tablets, to inform the consumer about the newest offers or products.

The portal architecture of the present system is designed in a way such that a dynamic enlargement of the number of the consumers is possible. The system is in preferred embodiments characterised by improved usability, accessibility, scalability, expandability, adjustability and security compared to presently known systems.

System Structure:

The system structural backbone is a preferred defining feature of the system and includes the entire suite of system modules with their specific characteristics. The modules, present in the system as specific software modules configured for carrying out their appropriate functions, are divided into core and peripheral modules. The core modules are in some embodiments required for the operation of the platform. Optional core modules may be present in preferred embodiments. The peripheral modules provide the system with the care functions or administrative functions (billing, logging, In/Export, Reporting, Administration, and so forth). The series of modules are first validated on the platform and may be extended by additional modules.

FIG. 1 provides a general overview of the system and FIG. 2 provides a preferred embodiment of the sequential representation of the process encompassed by the system and method of the present invention. FIG. 3 shows a preferred representation of the system structure of the modules.

TABLE 1

Module overview

| Core Modules | Optional (core) Modules | Peripheral Modules |
|---|---|---|
| User Profile 5 | Trending 6 | User Care 16 |
| Scan 1 | Style 7 | Provider Care 17 |
| Product Profile 10 | Community 8 | Sales Reporting 18 |
| Production Profile 12 | Messaging 11 | Logging 19 |
| Sales Match 3 | Rewards 13 | Billing 20 |
| Sales Tools 2 | Analytics 14 | File Import/Export 21 |
| Configurator 4 | Predictions 15 | Administration 22 |
| Ordering 9 | | Business Care 23 |

TABLE 2

Overview of the modules and the preferred information connections and relationships between the various modules as shown in the figures and in preferred embodiments.

1 Scan 1.1 3D Geometry acquisition, recognition and/or transmission
1.2 Augmented/Virtual Reality
1.3 DBMS Transfer to 5.3 from 1.1
1.4 Object recognition from the product profile
1.5 Potential connection to all other core or optional core modules 2 Sales Tools 2.1 Create Consumer/user Profiles, data to 5
2.2 Shop area incl. sale support functions (module connected to 6, 7, 8)
2.3 Integrated in 1, 4, 9
2.4 Shopping cart, Wish list, Notepad
2.5 Review and Rating 3 Sales Match 3.1 Adjustment from 5 to 10
3.2 Product proposal based on 5, 6, 7, 9, 10, 13, 14, 15
3.3 Adjustment from 1.4 and 10
3.4 Adjustment with Communities 4 Configurator 4.1 Selection and visualization from the product profile 10
4.2 Visualization at the body (AR)
4.3 Release/Presentation of all modification parameters (10.4, 10.5)
4.4 Alternative suggestions based on 5, 6, 7, 9, 10, 13, 14, 15

TABLE 2-continued

Overview of the modules and the preferred information connections and relationships between the various modules as shown in the figures and in preferred embodiments.

5 User Profile 5.1 Meta data
5.2 Payment data
5.3 Body data (Scan/Direct)
5.4 Ethnical data
5.5 min/max Values
5.6 myStyle, saved preferences
5.7 Integration Social Media Accounts
5.8 myConfig/Designs, saved preferences
5.9 Reward points, connection to 13
5.10 Connections to 14, 15

6 Trends 6.1 External input Product rating
6.2 From entire system, connections to 7, 8, 11, 14, 15
6.3 From 1.4
6.4 Display at Product rating 7 Style 7.1 External input via Style Matrix
7.2 From entire system, connections to 14, 15, 6, 7, 8
7.3 Style Matrix, based on a reference table 8 Community 8.1 Social Media (e.g. Facebook, twitter, google)
8.2 Blogs
8.3 Brands Services
8.4 connections to 6, 7, 11, 14, 15

9 Order 9.1 Settlement with Payment Service Provider
9.2 Payment option depending on the configuration (4)
9.3 Handover to OEM, Logistics and Retailer
9.4 Inventories
9.5 Order history (Consumer; All and Retail)
9.6 Delivery address and delivery time
9.7 Overview and Order confirmation
9.8 Returns processing
9.9 Credit vouchers, points and rebates, connection to 13

10 Product Profile 10.1 Meta data (Material, Colors, Article, Performance)
10.2 Geometrical data
10.3 Price (min/max)
10.4 Configurable parameter
10.5 List of compatibility (Material)
10.6 Rating
10.7 Star Style/Trends
10.8 Style Matrix
10.9 Type of product
10.10 Connections to 1, 2, 3, 4, 5, 9, 14, 15
10.11 Connection to production parameters/capabilities (FIG. 4), production profile 12

11 Messaging 11.1 Order information and confirmation
11.2 Shipping info
11.3 Newsletter and Offers from 2, 6, 7

12 Production Profile 12.1 Inventories
12.2 Production instructions
12.3 Automated manufacture control 13 Reward 13.1 Point system
13.2 Reward from sales, Style, Blogs, reviews and Scan
13.3 Link to other Loyalty programs 14 Analytics 14.1 Recording information on e.g. user location, interest, orders and/or customization
14.2 Identifying correlations between 14.1 and data from the user profile TABLE 2-continued Overview of the modules and the preferred information connections and relationships between the various modules as shown in the figures and in preferred embodiments.

14.3 Suggestions to user and/or provider of products according to said correlations
15 Predictions 15.1 Correlate information on local events, such as sports/musical events, from weather services, market, style and/or medical trends with user behavior
15.2 Transmit correlations to providers and/or users as product suggestions/predictions

TABLE 3

Overview of the modules and the preferred functions

| Core function for the prototype system | Module |
|---|---|
| Save Scanner data in newly defined data model in Profiles Consumer<br>Storing Consumer recorded foot geometry data<br>Using simple measurement (manual data entry) | Scan |
| Registration of an account/consumer profile<br>Targeted product search filtering criteria (color, size, . . . )<br>Automated recommendation of products based on external trends<br>Further purchase recommendations based on external consultants Shopping Cart<br>Separate carts for Multi-Retail system - max. 2 providers (eshop & Real shop)<br>Ordering procedure<br>Review the user data<br>Configurator with Augmented Reality<br>Provide offer to the user<br>Consulting directly in the store<br>Augmented Reality to support/Visualization of the product on the Consumer | Sales Tools |
| Compare the user profiles with the Product profiles during product selection (for example, based on geometry/geometric characteristics/Performance)<br>Sales Match can also be used to obtain further proposals on the basis of trends, style and previous orders in the product mask | Sales Match |
| Graphically supported tool to modify the product on the basis of certain configurable rules (material, color, options on the product selected)<br>Alternative Configuration suggestions based on consumer profiles Styles; Novelties | Configurator |
| Personal data<br>Account/Payment data<br>Social Media data<br>Reward data<br>Body data<br>Product data<br>Ethnical data<br>Personalized Style/Design data<br>The relevant Sales Configurator match and data is collected in the consumer profiles | User Profile |
| Targeted Marketing, adapted to the consumer behavior<br>Consideration of product Rating | Trends |
| Offer of products of similar/comparable Styles<br>Input of style combinations and alternatives | Style |
| Transmission of order to production machine<br>Record order histories based on the user and providers<br>Invitation to indicate the method of payment<br>Overview And order confirmation | Order |
| Product Profile Module provides the basis for a comparison to the consumer profiles to produce and implement options for the user<br>Comprehensive description of the characteristics of the products (performance, geometry, materials, products, customizability) | Product Profile |
| Provides communication to the user from the functional core processes in the form of authentication, notifications or service transactions<br>Is the gateway to all communication channels<br>Archiving all outgoing messages based on a user profile<br>Ensures notification of order infos and confirmation | Messaging |
| What capabilities does a producer have for any given product<br>Which Products/Product Designs can be delivered or produced | Production profile |
| Provides a connection between providers and the various system modules, enabling the providers to administer the contents of the corresponding modules, which are assigned to the respective products or providers | Business care |

TABLE 3-continued

Overview of the modules and the preferred functions

| Core function for the prototype system | Module |
| --- | --- |
| Access to all workflows and user accounts and Profiles<br>Administration of access and editing rights to the modules via Customer Care and Business Care<br>Adaptation of workflows, Business Care content, User Accounts and profiles<br>Regulate outgoing or parallel contact with the user via module Messaging<br>View all user traffic<br>Full access to platform (view and change), to all modules, workflows and accounts for error analysis, bug-fixing, patches, software updates | Administration |
| Processing of all invoice-relevant data<br>Create invoices for Consumer<br>Create Invoices for Business Partners/providers (Retailers, scanner suppliers, logistics partners etc.)<br>Triggering of sending invoices via the modules Messaging<br>Processing of incoming payments and automated trigger of payment reminders<br>Documentation of all claims and payments in accordance with the Accounting Directives<br>Verification and traceability of all invoices<br>Revision of invoices | Billing |
| Transfer and exchange of all relevant information about the product profiles and scanner profiles<br>All file exchanges are to be recorded in the form of a file transfer database and visualize separation in Business Care according to the defined client | File Import/Export |
| All data in the Consumer Profiles<br>Self-created Styles<br>All past sales and invoices<br>Notepad and prepared shopping carts<br>Current sales<br>Blogs (user stories) and recessions<br>Communities and communication with communities through messaging modules and Social Media channels<br>Contacting the customer (via modules Messaging)<br>Release of consumer profile data, Styles, Wishlist or sales made to other Users | User Care |

The modules of the system are described in more detail below:

User Profile (5):

The Module "User profile" (alternatively referred to as a consumer profile) collects all important personal Consumer/User relevant data. Up to date data security standards are considered when the data is transferred and stored into the DBMS. The installed data bases are preferably available from and/or distributed to all continents, to ensure an appropriate bandwidth and performance level. The user can create, extend or modify their profile at any place and time. These modifications from the respective profile can be realized by the user via the website or with a corresponding application. In this case, the consumer may access via a private terminal or via a public accessible portal (for example in a Store).

The profile data preferably comprises:
Personal data
Account/Payment data
Social Media data
Reward data
Body data
Product data
Ethnical data
Personalized Style/Design data The data of the user has to be transmitted into the system user database. The transmission can be realized either manually (by using the keyboard) or it can be transmitted automatically via different technologies, for example directly from a body scanner.

The consumer enters the system website or app and will be guided in a logical sequence through the registration process. The mandatory data are the personal data, body data and the account data. The optional data are Social Media data, ethnical data, product data, reward data and the Style/Design data.

The offered products are regulated by the partner companies (providers) who are connected to the system. After product selection from the user, this product can be purchased as a standard product or can be modified by the consumer by the means of design or performance according to the configurator. The scope of the modified elements of each product are determined by the partner company (provider) based on manufacturing capabilities, since only the partner company can verify the key characteristics and manufacturing capabilities for each product. If there is an individual modification of the product (design, performance), a new product configuration has been created. This new configuration will be transmitted to the connected partner company (provider), who then manufactures the product according to the specific modifications.

Product Profile (10)

The module "Product Profile" represents the products from the connected partner companies (providers). Each partner company is responsible for definition of the product and which configuration possibilities will be shown in the system portal. The partner company needs to locate the min/max values for the modifications, e.g. Sizes, materials, colors, performance values, etc. The body data, generated by the user, are used to identify the optimal products based on these basic characteristics in the product profile.

The basic data to be included in the profiles are divided into Product Design Data and in Product Metadata, otherwise termed a manufacturing profile. All important information to manufacture the product in its original version are located within the Metadata. Possible modification of the product is deposited within the Design data. It is possible to select a standard product and purchase it without doing any modification. Modification is preferred.

For example, the manufacturer (provider) may enable adjustment of the performance of the shoe by e.g. the modifying the sole properties. This adjustment could be realized by using a corresponding detection of the running profile and their evaluation.

Production Profile (12)

A module "Production Profile" comprises the necessary information from the connected partner companies (providers) designating that a partner company can have one or more production facilities in different locations. Each product can be assigned to one or more production facilities. The assignment of the product manufacturer is carried out by the partner company (Brand and/or manufacturer) and is available in the system portal. The brand of each product has to ensure that the production facility has the necessary capacity to manufacture the incoming orders. The Profile Production is preferably divided into two separate categories: General data and Skills. Category "General data" consists of all relevant data which is necessary to determine the production facility that is capable of manufacturing the ordered product. Category "Skills" contains all relevant information about the level of performance from each individual production facility. The level of performance means that products can be manufactured in this facility and what possible modifications are feasible.

If an order has been placed in the system portal, this order may be associated with a production facility, which is qualified for the manufacturing of the product. Before ordering the product the product, manufacturer has to feedback to the system portal regarding the necessary information such as the product price and delivery time. This information is preferably independent of the product status, by the means of a standard product or an individualized product. The production facility has to ensure that all necessary materials to manufacture the product are in-house and available at all times. The warehouse planning as well as the production planning are in the responsibility of the production facility.

If the case occurs that one product can be manufactured at different independent production facilities, the brand of the product needs to make the decision which production facility receives the order. Decision aids for the brand can be price, delivery times, quantity of orders etc. It will be the Brands decision to create a ranking system for their production facilities or how the orders will be placed.

FIG. 4 provides a schematic representation of the subdivision of the production profile and data comprised therein.

Ordering (9)

The overall function of the Module "Ordering" is the administration of all financial transactions coming from the consumer or partner company. When the consumer has made the final selection of the product and is aware of all necessary payment information like product price and delivery time, the order can be accepted. This acceptance is then forwarded with all product information's to the production facility. During that process, the order gets a unique Order-Identification number, which is associated to the product(s) and to the consumer. When one order exists with more than one product, the total value of goods needs to summed up and has to be transferred into one price. It is possible that different products out of one order can be manufactured in different production facilities. Each ordered product obtains a unique Production-Identification number in order to identify the order with the production facility.

Finally, the total order receives a unique invoice number, which has to be transferred to the consumer for payment actions. After the purchase has been completed, the Order Module creates an Order-Overview including with an Order-confirmation.

The Ordering module is organizing the settlement of payment with a service provider and arranges the payment transfers to the partner companies (providers), according to the negotiated conditions. If all payment transactions has been approved (Consumer is solvent), the goods can be sent to the consumer, whenever the production of the product is completed. The Ordering module is transferring the Address and delivery data to a selected logistics provider, which then can take the goods from the manufacturer. If it occurs that one or more products must be returned, the ordering module handles the processing of returns.

Scan Module (1)

The Module "Scan" enables the acquisition and/or administration of the technical determination of the Body data from the user and the Product data for the offered products from the partner companies. The Body/Product Data will be available as 2D generated data and/or as a 3D model. In the context of the present invention, the Body/Product Data may, amongst other things, be referred to as geometric characteristics of a user's body or parts thereof. The technical determination of these data could be carried out manually (2D) or technically (2D, 3D) by using corresponding measuring technologies. Many different technologies are already available to detect the body data easily and very convenient for the consumer.

To realize the integration of the scanning technology, a technical interface to connect the hardware with the software of all partner companies needs to be defined. This interface translates the generated 2/3 D data into standard file designations, so that the content of this data is understandable for the system portal.

The further process provides the integration of the data from the scan module into the Product Profile. In a simple case this would be, for example, a determination of the size or contours of a foot, whereupon the Sales Tools can propose to the consumer the ideal matching product in light of the product profiles from the product database. In preferred embodiments an extended function integrates the running or other dynamic foot or body information from the user into the user profile. If the running or walking data is matched with the product profile the manufacture of a total customized sole for the consumer is possible. The modifications can be carried out automatically, related to the prior determined characteristics and data regarding each product from the Brand (provider). The transmitted Body/Product data will be stored in the user profile.

Configurator Module (4)

The "Configurator" module allows the consumer an individual adaption from the selected product to the specific needs to the consumer. The adaptions to the product are subject to certain rules which must be determined by the provider for any given product determined on manufacturing and customization capacity. These rules have to be provided to the portal before product released.

An adaption or customization can be simply a modification from the color of the product or product elements. It also could contain a modification from the performance values of the product based on size, shape, material, weight, density, and so forth. These performance adaptions need to be qualified by the provider and set as min/max values related to the product. To support the changes, an appealing presentation of potential customizations is envisaged. Furthermore, the user may obtain additional product information, which can contain similar products comparable to the selected product.

Information from the modules Style and Trends in the module Configurator are included, providing a broader range of information to the consumer. If a product configured by the consumer in accordance with the ideas (Style, color) and the needs (performance) similar products based on the consumer profile will be visualized and offered in addition to this product. If the user selects during the process of configuration further new characteristics of the product which are at the moment unknown, these new characteristics can be recorded in the user profile and/or product profile and may be used as subsequent purchase options. The module "Configurator" can additionally be supported by technologies such as augmented reality or virtual reality options in order to enhance the shopping experience.

Sales Tools Module (2)

The Module "SalesTools" is preferably a superordinate unit, which acts at the Frontend of the system portal to the user. Sales Tools organizes the logical flow when a consumer enters the system portal to purchase a product. The Sales Tools module makes it possible to create a profile and configure it appropriately via the user profile. SalesTools integrates the Modules Scan, Configurator, Order, Style, Trends, Community, Smart Data, Messaging, Predictions and Reward. The sales tools module may also function in the background organizing interaction and communication between these modules with each other.

The consumer finds in the SalesTools Shop area either free and/or targeted product search options. The product search is supported by the features specified in the user profile, like personal information (sizes, styles, specifications, brands, and so forth). The pre-selection according to the specified profile is presented to the user in addition to the standard product.

SalesTools operates together with the Module SmartData during the product search, which simplifies the preselection of products for the consumer. By doing that, an automated purchase recommendation to the consumer is created, based on previous purchasing events of the user or of other users. Further options within SalesTools is the shopping cart, wish list or notepad with a non-purchase Memory function.

Messaging Module (11)

The Module "Messaging" takes care of all communication tasks. Messaging communicates to the user as well as to the other installed Modules. It is possible to use different communication channels. The choice of the communication channel has to be decided according to the occasion. Sensitive data, like Account information's, reminders or Ordering are transferred via a secured communication channel, e.g. via Email or post letter. The messaging module ensures notifications of ordering information, an order confirmation, the delivery of the product information and possible payment reminders. All sent information to the user are stored as an isolated client. The filing of the stored data needs to be understandable by using the Consumer ID which is assigned to the specific consumer.

Reward Module (13)

The "Reward" module acts as a function of a point system, which is oriented to the purchases from the consumer. The more purchases are made, the higher is the Reward Account. Only for real made purchases points are awarded.

SalesMatch Module (3)

The "SalesMatch" module enables matching between the user profile and the product profiles during the purchase process. "SalesMatch" continuously compares the content from the user profiles and/or "Configurator" with the existing data from and product profiles.

Possible matching values relate to sizes, performance values, body geometries, colours, styles, and so forth. The matching form the above values leads the consumer to a much more precise and better fitting product with less chance of any dislike, discomfort or other reasons for rejection. Thus, it will no longer be necessary for the consumer to choose any of these values by themselves out of a drop box or other selection possibility, because "SalesMatch" takes care of these actions automatically. SalesMatch is also offering similar products, which are similar to the matching process. Sales Match can also be used to indicate other product proposals on the basis of Trends or Styles and highlight these products to the consumer.

Another function inside the Module "SalesMatch" is the photogrammetric object recognition (POR). By using this POR functionality a camera from a Smartphone or Tablet PC identifies objects where the camera is held on it and compares the Photo object with the geometric data from products existing in product DBMS. If a product has been found and is matching with the user profile values of the consumer, it can be purchased.

Analytics Module (14)

The module "Analytics" enables analysis of incoming data from consumers and/or from the market and interprets these data into different segments. Preferred segments are for example consumer behavior, market development, style and trend development for the diverse wearable and/or medical items. In preferred embodiments the analytics module obtains data primarily from all Core Modules (See FIG. 3), as well as from some optional modules such as "Community", "Messages", "Style", "Trends", "Design" and "Reward".

By analyzing the "traffic" (consumer behavior with respect to purchases and/or product interest) on the platform and especially the individual user traffic, it is possible to present specific customized advertisements to the consumer. Besides that the use (Search, Select) of the website or the platform has to be identified. In preferred embodiments "Analytics" is a "Self-Learning" software module.

In case of major social events, such as sports or promotion events in the geographical proximity of any given user, increasing traffic can be localized and assigned to the specific event. The Analytics module therefore enable the general performance of the website/platform to be analyzed to ensure the best possible performance for the user. All collected data may preferably be summarized into reports in order to find out where the potential for improvement of the platform is. Connected partner companies (providers) can in some embodiments use the collected data to analyze purchase of goods.

Predictions Module (15)

The module "Predictions" obtains its data from the module "Analytics", and from "Smart data" or "Big data", preferably from different online channels and also from actual online discussions via Social Networks (e. g. via community, messaging, trends modules). The predictions module's function is to carry out data mining and derive from this collected data new strategies for product proposals or suggestions for products or product optimization/customizations.

The preparation of the data mining provides new strategies (product proposals or suggestions for products or product optimization/customizations) which can be forwarded to the connected partner companies (providers) for e. g. adjusting product manufacturing capabilities or adjusting product profiles. A possible scenario could be: Users, who buy brown leather shoes will buy after three weeks trousers, fitting to the shoes.

The "Prediction" software module will enable prediction of such consumer behaviour and is capable of forwarding the predicted user behaviours to relevant connected partner companies (providers) who can schedule their production services (e. g. via product and production profiles) accordingly. Also, by way of example, the user can receive advertisements in advance in order to order a custom-fit trouser during the shoe acquisition. The "Prediction" module functions based on collected data of the individual behavior of the user and/or from external sources such as mentioned herein and suggests possible other wearable and/or medical products during use of the system described herein to users and/or provicers.

Example Relating to Manufacture of a Shoe Sole

Information from any given order is transferred to a manufacturing device. Said information comprises preferably the digital representation of a foot or part thereof of a user, in particular geometric characteristics of the digital representation of a foot or part thereof of a user.

The manufacturing device is preferably shoe manufacturing device, for example here an injection or molding device.

FIG. 5 shows a cross-section view of a device for creating a sole, which is generally designated by the reference numeral 71. This device consists of a injection unit in the form of a mixing head 2, which is provided substantially of a housing 73, in which a tapered screw 74, and a mixing screw 75 is disposed rotatably and translationally movable in the tapered screw 74. According to the taper of the screw chamber 74 also this screw 75 is conical, which extends the conical screw to a nozzle mouthpiece 76. The nozzle mouthpiece 76 is applied to a sprue runner 77 of a molding tool 78, consisting of two side molding elements 79 and a base stamp 80. In the present example the cavity 81 formed by the side molding elements 79 and the base stamp 10 is limited at the top by a block 83 upholstered with a shoe upper 82.

At the end of the screw chamber 74, which is at the opposite side of the nozzle mouthpiece 76, supply channels 84 open into the feeding system for a thermoplastic base material and of additives to be blended to the base material. The base material and the additives are introduced via a valve arrangement (FIG. 10) into the screw chamber 74, wherein the valve assembly is radially disposed around the screw chamber 74. A1 and B1 denote the valves, which are responsible for supplying the thermoplastic material, while references C1 to C6 denote the valves, which are responsible for supplying the respective additives.

As further apparent from FIG. 5, in this case the sole produced by injection molding is virtually divided into the segments 1 to 3. Such multi-section injection leads to tailored shoe sole production according to the characteristics of the user's foot. In light of 2D or 3D scan data, the characteristics of the sole can be determined, for example that differently characterised injection material is used in the forefoot, arch and heel regions of the sole, thereby providing different properties of the sole in these or other regions. For example, the position of the arch can be identified by scan data, which can be transmitted to the manufacturing device, thereby determining the size and shape of the arch region of the shoe sole, which is manufactured using computer-controlled automated multi-zone injection means, preferably as described herein. As a further example, the 2D or 3D scan data can provide information on pressure distribution of the foot, and as such this information can be processed by the computer controlled injection molding device to employ materials in particular regions of the sole of according characteristics, for example using harder or software sole material as is required in particular zones, according to the user's foot.

By changing the flow rate in the mixing head 72 the individual segments are supplied with the formulation of base material and appropriate additives selected for each segment.

FIG. 6 shows the alternative casting method. Here, the mixing head 72, which is preferably identical to the mixing head 72 of FIG. 5, is arranged vertically above the open mold cavity 81. This cavity is virtually divided into three sectors, too. The material formulation selected for each sector is throughput independently poured along a track or route 86 into the cavity 81, starting at the left. The casting occurs in one shot, wherein each sector is given the appropriate formulation.

FIG. 8b shows a shoe sole produced by the apparatus of FIG. 1 in plan view and FIG. 8a shows the same shoe sole in section view. The virtual division of the sectors is realized by the injecting process.

In FIG. 8c a shoe sole is displayed, which has been manufactured according to the manufacturing process with the apparatus of FIGS. 6 and 7 respectively. This indicates that even spots are possible.

FIG. 9 shows a schematic representation of a so-called additive rack or device, which is identified by reference 87. It consists of a frame 88, on which all the hardware and the electric control 89 for metering and feeding of the respective required additive is arranged.

The hardware consists of a metering pump 90, a temperature-controlled pressure vessel 91, the temperature control unit 92 and a hose 93, which is connected with one of the valves, which are illustrated in FIG. 10. Not displayed is the communication line to the corresponding injection molding machine or a wire to the power supply.

This additive cart (rack or device) forms an autonomous unit, which can be prepared for the corresponding application in advance and can be quickly connected to the injection molding machine in case of need.

The screw 5 is also provided with a drive for its translational movement. In addition to the conveying property, this drive together with the rotary drive is also responsible for the cleaning of the mixing head. After several filling processes, the speed of the screw can be greatly increased (up to 18,000 rev/min). In doing so, the screw moves towards the nozzle mouthpiece, the screw flights are driven against the inner wall of the screw chamber and thus material residues are scraped and the material located in the screw is ejected.

Finally, FIG. 11 shows possible combinations of a base material and various additives are displayed.

The invention claimed is:

1. A system for customized manufacture of a wearable and/or medical product, comprising:
   a scanner configured to store and transfer a digital representation of a body or part thereof of one or more users,
   a manufacturing unit of one or more providers, wherein said manufacturing unit is configured to manufacture said wearable and/or medical product in accordance with geometric characteristics of said digital representation, and
   a customized product selection platform comprising:
   a) one or more computing devices,
   b) a user database comprising the digital representation of a body or part thereof of one or more users,
   c) a product database comprising a digital representation of one or more products, stored as a product profile, for customization by one or more providers, d) a matching and/or configurator engine including computer-executable software configured for identification, selection, and customization of said product from said product database for customized manufacture according to the digital representation of a body or part thereof of one or more users, and e) data connections enabling transfer of data between (i) said scanner and said user database, (ii) said user database and said matching and/or configurator engine, (iii) said product database and said matching and/or configurator engine, and (iv) said matching and/or configurator engine and said manufacturing unit, wherein the matching and/or configurator engine is configured to compare the geometric characteristics of the digital representation of a body or part thereof and the digital representation of one or more products stored in the product database, wherein the matching and/or configurator engine is further configured to transmit the identification, selection, and customization of said product to the manufacturing unit thereby causing said manufacturing unit to manufacture the wearable and/or medical product.

2. A system according to claim 1, wherein the geometric characteristics are selected from a group consisting of body height, 3D geometries of the full body, foot geometries, head dimensions, eye separation distance, torso size, torso shape, hand geometry, or anatomy.

3. A system according to claim 1, wherein the geometric characteristics comprise individual specific physical properties of the user's body including at least one of foot pressure, gait, height, girth, body shape or weight.

4. A system according to claim 1, wherein the geometric characteristics are selected from a group consisting of foot shape, form, and/or motion, pronation or supination.

5. A system according to claim 1, wherein the geometric characteristics comprise additional data on the user's body weight, body sway, limb length discrepancy, gait cycle events, pronation and supination events and body mass migration.

6. A system according to claim 1, wherein the product database comprises an electronic representation of one or more of said products for customization.

7. A system according to claim 6, wherein the electronic representation comprises a product profile comprising information on customizability of the product which are selected from a group comprising size, shape, density, softness, form, texture, colour or weight of the product or parts thereof.

8. A system according to claim 1, wherein the scanner comprises a computing device upon which a digital representation of a body or part thereof of one or more users is stored and transmitted to said user database.

9. A system according to claim 1, wherein the scanner comprises or is connected to a scanning device configured for generating a 2D or 3D digital representation of the body or part thereof of a user.

10. A system according to claim 1, wherein the digital representation of the body or part thereof of a user comprises one or more computer data files comprising information that represents the outer surface of the body or part thereof of a user obtained from 3D scanning.

11. A system according to claim 1, wherein the user database comprises for each user a user profile, said profile comprising information on one or more physical and/or geometric characteristics of the user, selected from foot size, foot shape, user height, weight, physical activity and/or medical conditions.

12. A system according to claim 11, wherein the user profile comprises information on previous product selection and/or interest, purchasing history, past and/or present location, a user identification number, delivery address, preferred colours, brands and/or shoe prices, language.

13. A system according to claim 1, wherein the customized product selection platform comprises one or more computer-executable software modules configured to:
conduct ordering, payment and/or delivery procedures between said users and providers.

14. A system according to claim 1, additionally configured to:
provide product suggestions according to popularity of purchases and/or product interest by other users (trending), wherein said suggestions are selected and/or ranked according to information in the user profile including at least one of age, past and/or present location, preferred colours, brands or shoe prices.

15. A system according to claim 1, additionally configured for
providing product suggestions according to similarity in products to those according to previous product selection and/or interest of the user, wherein said suggestions are selected and/or ranked according to information in the user profile, including at least one of age, past and/or present location, preferred colours, brands or shoe prices.

16. A system according to claim 1, additionally configured to transmit data and/or at least one message between multiple users and/or transmit data and/or at least one message to social media platforms.

17. A system according to claim 1 comprising at least two or more providers, wherein each provider comprises one or more manufacturing units.

18. A system according to claim 1, wherein the customized product selection platform comprises one or more computer-executable software modules configured to record information on user location, user interest, user orders and/or customization selections, identify trends in said information including correlations between products for customized manufacture and data from the user profile, and make suggestions to a user and/or to a provider of customizable products according to said correlations.

19. A system according to claim 1, wherein the wearable and/or medical product comprises a shoe or part thereof and the digital representation of a body or part thereof comprise digital representation of a foot or part thereof.

20. A system according to claim 19 for customized manufacture of a shoe or part thereof, wherein the manufacturing unit comprises a shoe manufacturing unit that includes an injection, molding and/or pouring device for the manufacture of a shoe, shoe sole and/or shoe in-sole.

21. A system according to claim 20 for customized shoe manufacture, wherein the injection, molding and/or pouring device comprises a mixing head configured to mix multiple synthetic duroplastic and/or thermoplastic synthetic components including base materials and additives and distribute said components into a cavity including a shoe sole or in-sole.

22. A system according to claim 21, wherein the shoe sole or in-sole comprises multiple areas comprising different components and/or mixtures of components with particular physical properties in accordance with the geometric characteristics of said digital representation of the foot of a user.

23. A system according to claim 20, wherein a form or a molding form is configured to provide a particular shape of the injected material.

24. A computer-implemented method for selection of a wearable and/or medical product for customized manufacture, comprising:
- providing a digital representation of the body or part thereof of one or more users in a scanner including a computing device, said device being configured for storing and transmitting said representation,
- transmitting said digital representation of a body or part thereof to a user database of a customized product selection platform, wherein said platform comprises:
  a) one or more computing devices,
  b) a user database comprising the digital representation of a body or part thereof of one or more users,
  c) a product database comprising a digital representation of one or more products, stored as a product profile, for customization by one or more providers,
  d) a matching and/or configurator engine including computer-executable software configured for identification and selection, and customization, of a product from said product database for customized manufacture according to the digital representation of a body or part thereof of one or more users, the matching and/or configurator engine configured for a comparison of the geometric characteristics of the digital representation of a body or part thereof and the digital representation of one or more products stored in the product database, and
  e) data connections enabling transfer of data between (i) said scanner and said user database, (ii) said user database and said matching and/or configurator engine, (iii) said product database and said matching and/or configurator engine, and (iv) said matching and/or configurator engine and said manufacturing unit, and
- transmitting a product selection from said platform to a manufacturing unit of one or more providers and causing said manufacturing unit to manufacture a wearable and/or medical product in accordance with the geometric characteristics of the digital representation of a body or part thereof of a user.

25. The method according to claim 24, wherein said product is a shoe or part thereof and the digital representation of a body or part thereof is a digital representation of a foot or part thereof.

26. The method according to claim 25, wherein further comprising manufacturing said shoe or part thereof in accordance with the geometric characteristics of said digital representation of the foot or part thereof of the user.

27. The method for customized manufacture of a shoe or part thereof according to claim 25, wherein manufacturing said shoe or part thereof is performed by a shoe manufacturing unit that comprises an injection, molding and/or pouring device for the manufacture of a shoe, shoe sole and/or shoe in-sole, wherein the injection, pouring and/or molding device comprises a mixing head configured to mix multiple synthetic duroplastic and/or thermoplastic synthetic components including base materials and additives and distribute said components into a cavity including a shoe sole or in-sole, whereby said shoe sole or in-sole comprises multiple areas comprising different components and/or mixtures of components with particular physical and/or geometric properties in accordance with the geometric characteristics of said digital representation of the foot of a user.

* * * * *